US009572801B2

(12) United States Patent
Askew et al.

(10) Patent No.: US 9,572,801 B2
(45) Date of Patent: Feb. 21, 2017

(54) TETRAHYDRONAPHTHYRIDINYL PROPIONIC ACID DERIVATIVES AND USES THEREOF

(71) Applicant: SciFluor Life Sciences, Inc., Cambridge, MA (US)

(72) Inventors: Ben C. Askew, Marshfield, MA (US); D. Scott Edwards, Bedford, MA (US)

(73) Assignee: SciFluor Life Sciences, Inc., Cambridge, MA (US)

( * ) Notice: Subject to any disclaimer, the term of this patent is extended or adjusted under 35 U.S.C. 154(b) by 0 days.

(21) Appl. No.: 15/142,023

(22) Filed: Apr. 29, 2016

(65) Prior Publication Data

US 2016/0317527 A1 Nov. 3, 2016

Related U.S. Application Data

(60) Provisional application No. 62/154,894, filed on Apr. 30, 2015.

(51) Int. Cl.
| | | |
|---|---|---|
| *A61K 31/4709* | (2006.01) | |
| *A61K 31/444* | (2006.01) | |
| *A61K 31/4375* | (2006.01) | |
| *A61K 31/4178* | (2006.01) | |

(52) U.S. Cl.
CPC ....... *A61K 31/4709* (2013.01); *A61K 31/4178* (2013.01); *A61K 31/4375* (2013.01); *A61K 31/444* (2013.01)

(58) Field of Classification Search
None
See application file for complete search history.

(56) References Cited

U.S. PATENT DOCUMENTS

| | | | |
|---|---|---|---|
| 4,937,266 A | 6/1990 | Tomikawa et al. | |
| 5,374,660 A | 12/1994 | Murad et al. | |
| 5,571,846 A | 11/1996 | Murad et al. | |
| 5,645,839 A | 7/1997 | Chobanian et al. | |
| 6,017,926 A | 1/2000 | Askew et al. | |
| 6,117,445 A | 9/2000 | Neely | |
| 6,139,847 A | 10/2000 | Chobanian et al. | |
| 6,268,342 B1 | 7/2001 | Culler et al. | |
| 6,303,126 B1 | 10/2001 | Nakamura et al. | |
| 6,500,835 B2 | 12/2002 | Fukami et al. | |
| 6,664,227 B1 | 12/2003 | Wynn et al. | |
| 8,901,144 B2 | 12/2014 | Askew et al. | |
| 9,266,884 B2 | 2/2016 | Askew et al. | |
| 2002/0188001 A1 | 12/2002 | Xu et al. | |
| 2015/0057308 A1* | 2/2015 | Askew ................ | C07D 471/04 514/300 |
| 2016/0075698 A1 | 3/2016 | Askew et al. | |
| 2016/0130270 A1 | 5/2016 | Askew et al. | |

FOREIGN PATENT DOCUMENTS

WO  WO 02/22615  3/2002

OTHER PUBLICATIONS

Adams J. et al: "Structure Activity Relationships of $\alpha_v$ Integrin Antagonists for Pulmonary Fibrosis by Variation in Aryl Substituents", ACS Medicinal Chemistry Letters, vol. 5, No. 11, Sep. 19, 2014, p. 1207-1212.
Chen et al., "FIC1 and BSEP defects in Taiwanese patients with chronic intrahepatic cholestasis with low γ-glutamyltranspeptidase levels", *The Journal of Pediatrics* 140, p. 119-24 (2002).
Hahm K. et al. "$\alpha_v\beta_6$ Integrin Regulates Renal Fibrosis and Inflammation in Alport Mouse", *The American Journal of Pathology*, vol. 170, No. 1, Jan. 2007, p. 110-125.
Henderson et al., "Targeting of $\alpha_v$ integrin identifies a core molecular pathway that regulates fibrosis in several organs", *Nature Medicine*, vol. 19, No. 12, p. 1617-1627 (2013).
Henderson Neil C et al.: "Integrin-mediated regulation of TGF[beta] in fibrosis", *Biochim Biophys Acta*, vol. 1832, No. 7, Jul. 2013, p. 891-896.
Kumar et al., "Biochemical Characterization of the Binding of Echistatin to Integrin $\alpha_v\beta_3$ Receptor", *The Journal of Pharmacology and Experimental Therapeutics*, 283, p. 843-853 (1997).
Patsenker E. et al. "Inhibition of Integrin alphavbeta6 on Cholangiocytes Blocks Transforming Growth Factor-beta Activation and Retards Biliary Fibrosis Progression", Gastroenterology, vol. 135, No. 2, Aug. 1, 2008, p. 660-670.
Pilling et al., "Reduction of Bleomycin-Induced Pulmonary Fibrosis by Serum Amyloid P", *The Journal of Immunology* 179, p. 4035-4044, (2007).
Poynard et al., "Natural history of liver fibrosis progression in patients with chronic hepatitis C", *The Lancet*, vol. 349, p. 825-832 (1997).
Rognoni et al. "Kindlin-1 controls Wnt and TGF-β availability to regulate cutaneous stem cell proliferation", *Nature Medicine*, 20(4), p. 350-359 (2014).
Stragies, R. et al., "Design and Synthesis of a New Class of Selective Integrin α5β1 Antagonists", *J. Med. Chem.*, vol. 50, p. 3786-3794 (2007).
Truong et al., "Establishment of a standardized mouse model of hepatic fibrosis for biomedical research", *Biomedical Research and Therapy*, vol. 1, No. 2, p. 43-49 (2014).
Wayner et al., "Integrins αvβ3 and αvβ5 Contribute to Cell Attachment to Vitronectin but Differentially Distribute on the Cell Surface", *The Journal of Cell Biology*, vol. 113, No. 4, p. 919-929 (1991).

\* cited by examiner

*Primary Examiner* — Brian J Davis
(74) *Attorney, Agent, or Firm* — Cooley LLP; Heidi A. Erlacher; Chen Chen

(57) ABSTRACT

The present application relates to use of compounds of formula I for treating or preventing a fibrosis.

18 Claims, No Drawings

TETRAHYDRONAPHTHYRIDINYL PROPIONIC ACID DERIVATIVES AND USES THEREOF

RELATED APPLICATION

This application claims the benefit of and priority to U.S. provisional application No. 62/154,894, filed Apr. 30, 2015, the entire contents of which are incorporated herein by reference in their entirety.

BACKGROUND

Fibrosis is characterized by excessive accumulation of collagen in the extracellular matrix of the involved tissue. It is a long-standing and challenging clinical problem for which no effective treatment is currently available. The production of collagen is a highly regulated physiological process, the disturbance of which may lead to the development of tissue fibrosis. The formation of fibrous tissue is part of the normal beneficial process of healing after injury. In some cases, however, an abnormal accumulation of fibrous material can severely interfere with the normal function of the affected tissue or even cause the complete loss of function of the affected organ. Integrins are heterodimeric transmembrane proteins through which cells attach and communicate with extracellular matrices and other cells. αv integrins are key receptors involved in mediating cell migration and angiogenesis, and have been shown to be involved in a number of diseases and conditions, including fibrosis.

A variety of compounds have been identified as anti-fibrosis agents via different mechanisms of action, including the suppression of collagen expression. For example, pantethine (D-bis-(N-pantothenyl-β-aminoethyl)-disulfide) has been reported to be effective for the inhibition of hepatic fibrosis (U.S. Pat. No. 4,937,266). Also, a hydrazine derivative, benzoic hydrazide, has been shown to be a powerful antifibrotic agent (U.S. Pat. Nos. 5,374,660 and 5,571,846). In addition, angiotensin inhibitors are used in combination with nitric oxide stimulators to inhibit the progression of fibrosis (U.S. Pat. Nos. 5,645,839 and 6,139,847). Further, $A_1$ adenosine receptor antagonists and/or $P_{2x}$ purinoceptor antagonists are described for treating or preventing fibrosis and sclerosis (U.S. Pat. No. 6,117,445). More recently, somatostatin agonists, hepatocyte growth factors (HGFs), chymase inhibitors, and antagonists of IL-13 have been reported to effectively inhibit fibrosis (U.S. Pat. Nos. 6,268,342, 6,303,126, 6,500,835, and 6,664,227).

Thus, there continues to be a need for compounds, compositions, and methods for treating fibrosis, that are safe, effective, and conveniently administered. The present application addresses the need.

SUMMARY

The present application provides a method of treating or preventing a fibrosis, comprising administering to a subject in need thereof a therapeutically effective amount of a compound of formula I:

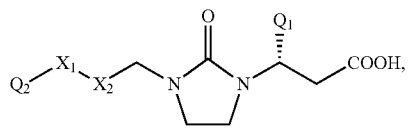

(I)

or a pharmaceutically acceptable salt or solvate thereof, wherein the compound of formula I is defined in detail herein below. In one aspect, the application relates to treating a fibrosis. In one aspect, the application relates to preventing a fibrosis.

The present application also provides the use of a compound of formula I or a pharmaceutically acceptable salt or solvate thereof in the manufacture of a medicament for the treatment or prevention of a fibrosis in a subject. The present application also provides the use of a compound of formula I or a pharmaceutically acceptable salt or solvate thereof in treating or preventing a fibrosis in a subject. The present application also provides a compound of formula I or a pharmaceutically acceptable salt or solvate thereof for use in treating or preventing a fibrosis in a subject.

Unless otherwise defined, all technical and scientific terms used herein have the same meaning as commonly understood by one of ordinary skill in the art to which this application belongs. In the case of conflict, the present specification, including definitions, will control. In the specification, the singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the present application. In addition, the materials, methods, and examples are illustrative only and are not intended to be limiting.

Other features and advantages of the application will be apparent from the following detailed description and claims.

DETAILED DESCRIPTION

The present application relates to a method of treating or preventing a fibrosis, comprising administering to a subject in need thereof a therapeutically effective amount of a compound of formula I or a pharmaceutically acceptable salt or solvate thereof.

The present application also relates to use of a compound of formula I or a pharmaceutically acceptable salt or solvate thereof in the manufacture of a medicament for the treatment or prevention of a fibrosis in a subject.

The present application also relates to use of a compound of formula I or a pharmaceutically acceptable salt or solvate thereof in treating or preventing a fibrosis in a subject.

The present application also provides a compound of formula I or a pharmaceutically acceptable salt or solvate thereof for use in treating or preventing a fibrosis in a subject.

Compounds of the present application are of formula I:

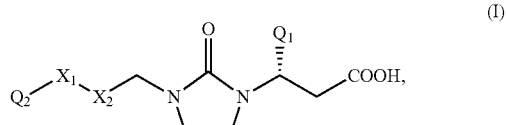

(I)

wherein:
$X_1$-$X_2$ is $CHR_1$—$CH_2$, CH=CH, or C(O)—$CH_2$;
$R_1$ is H or OH;

$Q_1$ is

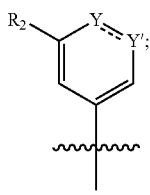

$Y=Y'$ is $CR_3=N$, $CR_4=CR_4$, or $C(O)$—NH;

$R_3$ is $C_1$-$C_3$ alkoxy, F, or $R_3$, together with $R_2$ and the carbon atoms to which they are attached, form a phenyl ring;

each $R_4$ is independently $C_1$-$C_3$ alkoxy, F, or two $R_4$, together with the carbon atoms to which they are attached, form a 5- or 6-membered heterocyclic ring comprising one or two heteroatoms selected from N and O;

$R_2$ is H or, together with $R_3$ and the carbon atoms to which they are attached, form a phenyl ring; and $Q_2$ is

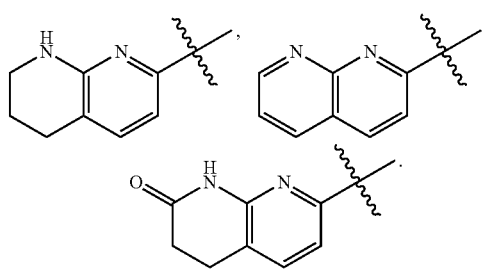

In one aspect, $X_1$-$X_2$ is $CHR_1$—$CH_2$. In a further aspect, $R_1$ is H. In another further aspect, $R_1$ is OH. In a further aspect, $R_1$ is (R)—OH. In another further aspect, $R_1$ is (S)—OH.

In one aspect, $X_1$-$X_2$ is CH=CH.

In one aspect, $X_1$-$X_2$ is $C(O)$—$CH_2$.

In one aspect, $Y=Y'$ is $CR_3=N$. In a further aspect, $R_3$ is $C_1$-$C_3$ alkoxy (e.g., methoxy, ethoxy, or propoxy). In a further aspect, $R_3$ is methoxy. In another further aspect, $R_3$ is F.

In one aspect, $Y=Y'$ is $CR_3=N$, and $R_3$, together with $R_2$ and the carbon atoms to which they are attached, form a phenyl ring.

In one aspect, $Y=Y'$ is $CR_4=CR_4$, and at least one $R_4$ is $C_1$-$C_3$ alkoxy (e.g., methoxy, ethoxy, or propoxy). In a further aspect, at least one $R_4$ is methoxy. In another aspect, one of $R_4$ is $C_1$-$C_3$ alkoxy (e.g., methoxy, ethoxy, or propoxy) and the other $R_4$ is F. In a further aspect, one of $R_4$ is ethoxy, and the other $R_4$ is F.

In one aspect, $Y=Y'$ is $CR_4=CR_4$, and two $R_4$, together with the carbon atoms to which they are attached, form a 5- or 6-membered heterocyclic ring comprising one or two heteroatoms selected from N and O. In a further aspect, two $R_4$, together with the carbon atoms to which they are attached, form a dihydrofuranyl, dihydropyranyl, tetrahydropyranyl, pyrrolidinyl, or piperidinyl ring. In a further aspect, two $R_4$, together with the carbon atoms to which they are attached, form a dihydrofuranyl ring.

In one aspect, $Y=Y'$ is $C(O)$—NH.

In one aspect, $R_2$ is H.

In one aspect, $R_2$, together with $R_3$ and the carbon atoms to which they are attached, form a phenyl ring.

In one aspect, $Q_2$ is

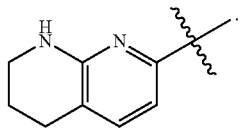 [SMILES: *c1ccc2c(n1)NCCC2]

In one aspect, $Q_2$ is

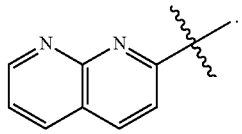 [SMILES: *c1ccc2cccnc2n1]

In one aspect, $Q_2$ is

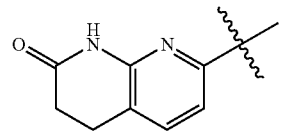

Any of the substituent groups illustrated above for any of $X_1$, $X_2$, Y, Y', $Q_1$, $Q_2$, $R_1$, $R_2$, $R_3$, and $R_4$ can be combined with any of the substituent groups illustrated above for the remaining of $X_1$, $X_2$, Y, Y', $Q_1$, $Q_2$, $R_1$, $R_2$, $R_3$, and $R_4$.

In one aspect, $X_1$-$X_2$ is $CHR_1$—$CH_2$; and $Q_2$ is

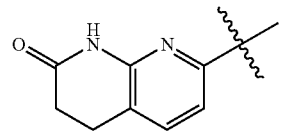

In a further aspect, $Y=Y'$ is $CR_3=N$. In a further aspect, $R_3$ is $C_1$-$C_3$ alkoxy (e.g., methoxy, ethoxy, or propoxy). In another further aspect, $R_3$, together with $R_2$ and the carbon atoms to which they are attached, form a phenyl ring.

In one aspect, compounds of the present application are of formula Ia:

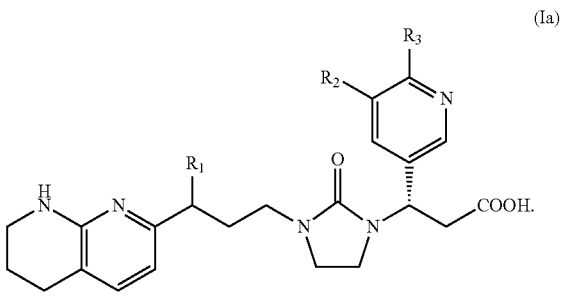

(Ia)

In a further aspect, $R_3$ is $C_1$-$C_3$ alkoxy (e.g., methoxy, ethoxy, or propoxy) and $R_2$ is H. In another further aspect, $R_3$, together with $R_2$ and the carbon atoms to which they are attached, form a phenyl ring. In a further aspect, $R_1$ is H. In another further aspect, $R_1$ is OH.

In one aspect, $X_1$-$X_2$ is $CHR_1$—$CH_2$; and $Q_2$ is

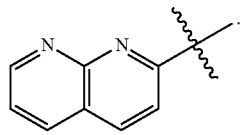 [SMILES: *c1ccc2cccnc2n1]

In a further aspect, $Y$ $=$ $Y'$ is $CR_3$ $=$ $N$. In a further aspect, $R_3$ is $C_1$-$C_3$ alkoxy (e.g., methoxy, ethoxy, or propoxy).

In one aspect, compounds of the present application are of formula Ib:

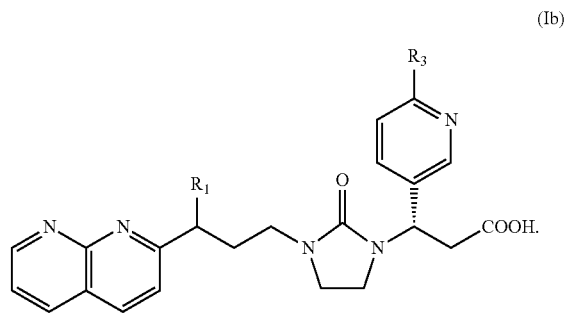

(Ib)

In a further aspect, $R_3$ is $C_1$-$C_3$ alkoxy (e.g., methoxy, ethoxy, or propoxy). In a further aspect, $R_1$ is H. In another further aspect, $R_1$ is OH.

In one aspect, $X_1$-$X_2$ is $CHR_1$—$CH_2$; and $Q_2$ is

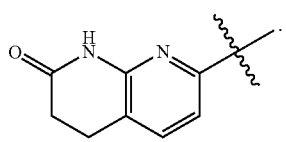 [SMILES: *c1ccc2c(n1)NC(=O)CC2]

In a further aspect, $Y$ $=$ $Y'$ is $CR_3$ $=$ $N$. In a further aspect, $R_3$ is $C_1$-$C_3$ alkoxy (e.g., methoxy, ethoxy, or propoxy).

In one aspect, compounds of the present application are of formula Ic:

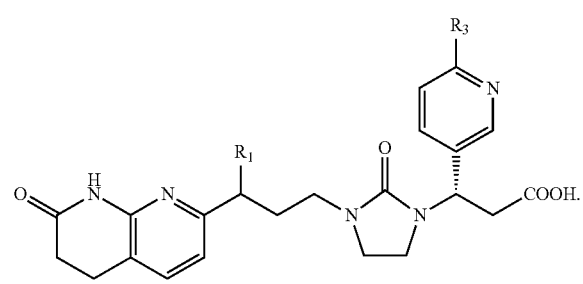

(Ic)

In a further aspect, $R_3$ is $C_1$-$C_3$ alkoxy (e.g., methoxy, ethoxy, or propoxy). In a further aspect, $R_1$ is H. In another further aspect, $R_1$ is OH.

In one aspect, $X_1$-$X_2$ is $CH$=$CH$; and $Q_2$ is

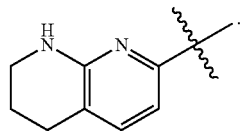 [SMILES: *c1ccc2c(n1)NCCC2]

In a further aspect, $Y$ $=$ $Y'$ is $CR_3$ $=$ $N$. In a further aspect, $R_3$ is $C_1$-$C_3$ alkoxy (e.g., methoxy, ethoxy, or propoxy).

In one aspect, compounds of the present application are of formula Id1 or Id2:

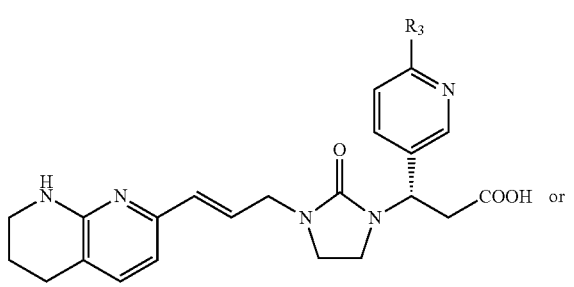

(Id1)

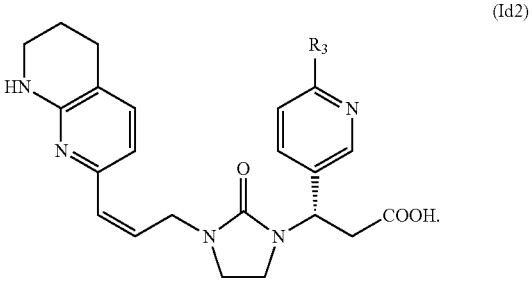

(Id2)

In a further aspect, $R_3$ is $C_1$-$C_3$ alkoxy (e.g., methoxy, ethoxy, or propoxy).

In one aspect, $X_1$-$X_2$ is $C(O)$—$CH_2$; and $Q_2$ is

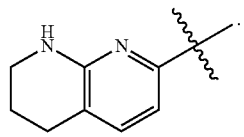 [SMILES: *c1ccc2c(n1)NCCC2]

In a further aspect, $Y$ $=$ $Y'$ is $CR_3$ $=$ $N$. In a further aspect, $R_3$ is $C_1$-$C_3$ alkoxy (e.g., methoxy, ethoxy, or propoxy).

In one aspect, compounds of the present application are of formula Ie:

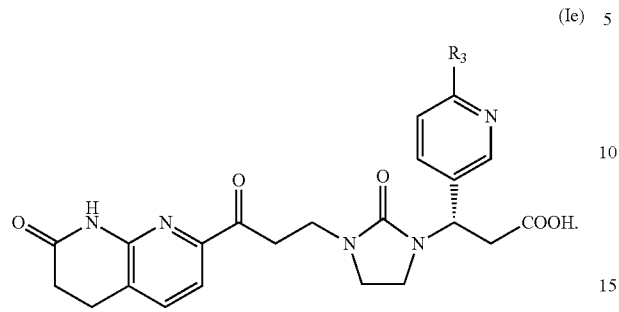

(Ie)

In a further aspect, $R_3$ is $C_1$-$C_3$ alkoxy (e.g., methoxy, ethoxy, or propoxy).

In one aspect, $X_1$-$X_2$ is $CHR_1$—$CH_2$; and $Q_2$ is

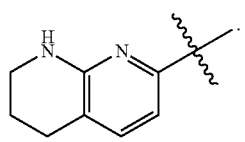 [SMILES: *c1ccc2c(n1)NCCC2]

In a further aspect, $Y \mathrel{\overset{\ldots}{=}} Y'$ is $CR_4$=$CR_4$. In a further aspect, one of $R_4$ is $C_1$-$C_3$ alkoxy (e.g., methoxy, ethoxy, or propoxy) and the other $R_4$ is F. In a further aspect, two $R_4$, together with the carbon atoms to which they are attached, form a 5- or 6-membered heterocyclic ring comprising one or two heteroatoms selected from N and O.

In one aspect, compounds of the present application are of formula If:

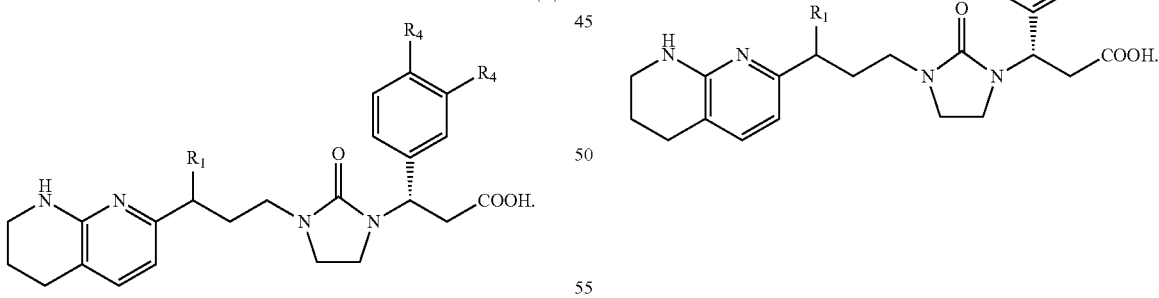

(If)

In a further aspect, one of $R_4$ is $C_1$-$C_3$ alkoxy (e.g., methoxy, ethoxy, or propoxy) and the other $R_4$ is F. In a further aspect, two $R_4$, together with the carbon atoms to which they are attached, form a 5- or 6-membered heterocyclic ring comprising one or two heteroatoms selected from N and O. In a further aspect, $R_1$ is H. In another further aspect, $R_1$ is OH.

In one aspect, $X_1$-$X_2$ is $CHR_1$—$CH_2$; and $Q_2$ is

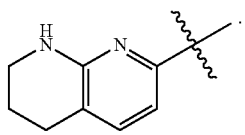 [SMILES: *c1ccc2c(n1)NCCC2]

In a further aspect, $Y \mathrel{\overset{\ldots}{=}} Y'$ is $C(O)$—NH.

In one aspect, compounds of the present application are of formula Ig:

(Ig)

In a further aspect, $R_1$ is H. In another further aspect, $R_1$ is OH.

Representative compounds of the present application for use in treating or preventing fibrosis include the compounds listed in Table 1 below.

TABLE 1

| Cmpd # | Chemical Structure | Name |
| --- | --- | --- |
| A1 | 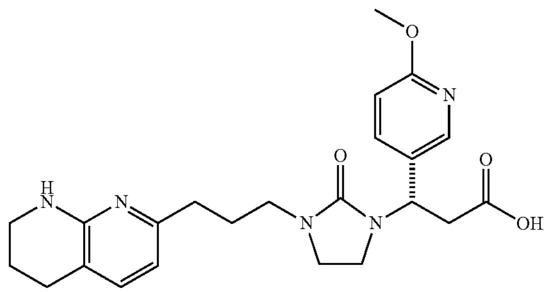 [SMILES: COc1ccc([C@H](CC(=O)O)N2CCN(CCCc3ccc4c(n3)NCCC4)C2=O)cn1] | (S)-3-(6-methoxypyridin-3-yl)-3-(2-oxo-3-(3-(5,6,7,8-tetrahydro-1,8-naphthyridin-2-yl)propyl)imidazolidin-1-yl)propanoic acid |
| A2 | 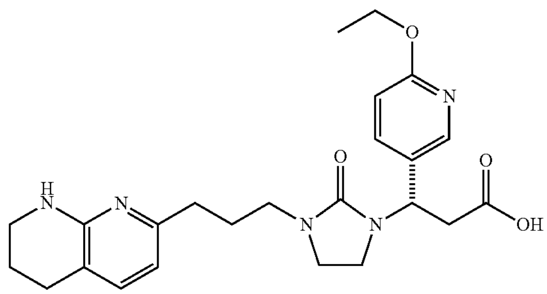 [SMILES: CCOc1ccc([C@H](CC(=O)O)N2CCN(CCCc3ccc4c(n3)NCCC4)C2=O)cn1] | (S)-3-(6-ethoxypyridin-3-yl)-3-(2-oxo-3-(3-(5,6,7,8-tetrahydro-1,8-naphthyridin-2-yl)propyl)imidazolidin-1-yl)propanoic acid |
| A3 | 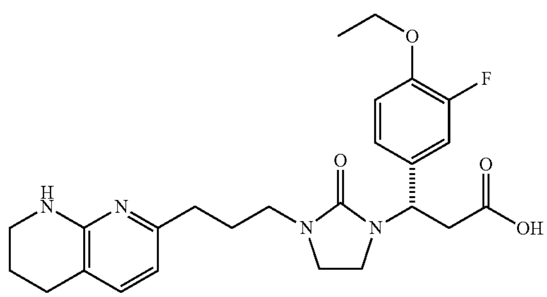 [SMILES: CCOc1ccc([C@H](CC(=O)O)N2CCN(CCCc3ccc4c(n3)NCCC4)C2=O)cc1F] | (S)-3-(4-ethoxy-3-fluorophenyl)-3-(2-oxo-3-(3-(5,6,7,8-tetrahydro-1,8-naphthyridin-2-yl)propyl)imidazolidin-1-yl)propanoic acid |
| A4 | 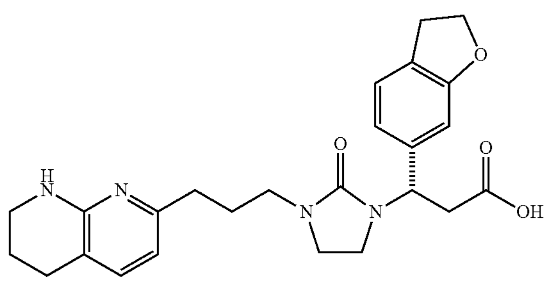 [SMILES: O=C(O)C[C@@H](c1ccc2c(c1)OCC2)N1CCN(CCCc2ccc3c(n2)NCCC3)C1=O] | (S)-3-(2,3-dihydrobenzofuran-6-yl)-3-(2-oxo-3-(3-(5,6,7,8-tetrahydro-1,8-naphthyridin-2-yl)propyl)imidazolidin-1-yl)propanoic acid |
| A5 | 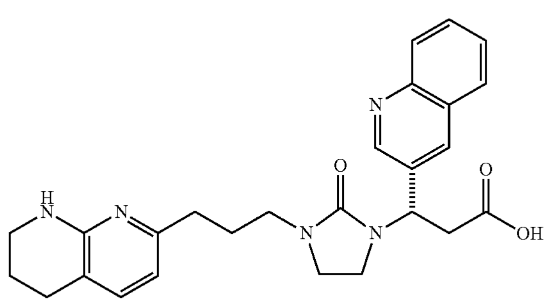 [SMILES: O=C(O)C[C@@H](c1cnc2ccccc2c1)N1CCN(CCCc2ccc3c(n2)NCCC3)C1=O] | (S)-3-(2-oxo-3-(3-(5,6,7,8-tetrahydro-1,8-naphthyridin-2-yl)propyl)imidazolidin-1-yl)-3-(quinolin-3-yl)propanoic acid |

TABLE 1-continued

| Cmpd # | Chemical Structure | Name |
| --- | --- | --- |
| A6 | 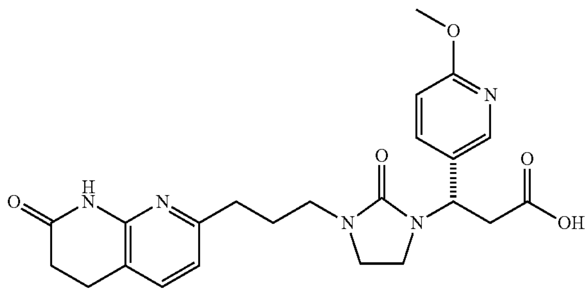 [SMILES: COc1ccc([C@H](CC(=O)O)N2CCN(CCCc3ccc4c(n3)NC(=O)CC4)C2=O)cn1] | (S)-3-(6-methoxypyridin-3-yl)-3-(2-oxo-3-(3-(7-oxo-5,6,7,8-tetrahydro-1,8-naphthyridin-2-yl)propyl)imidazolidin-1-yl)propanoic acid |
| A7 | 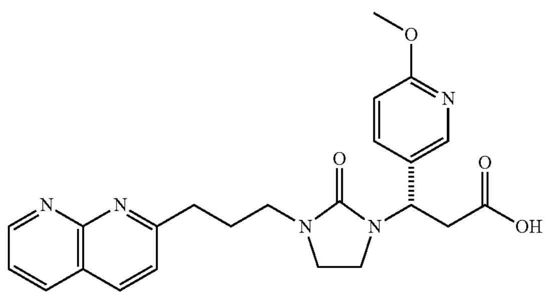 [SMILES: COc1ccc([C@H](CC(=O)O)N2CCN(CCCc3ccc4cccnc4n3)C2=O)cn1] | (S)-3-(3-(3-(1,8-naphthyridin-2-yl)propyl)-2-oxoimidazolidin-1-yl)-3-(6-methoxypyridin-3-yl)propanoic acid |
| A8 | 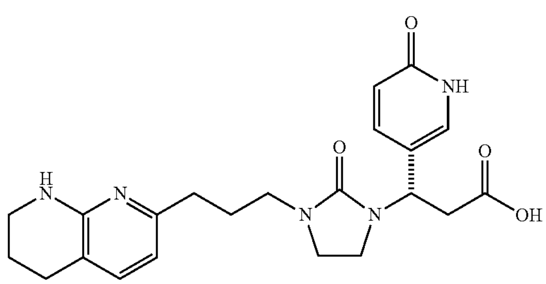 [SMILES: O=C(O)C[C@@H](c1ccc(=O)[nH]c1)N1CCN(CCCc2ccc3c(n2)NCCC3)C1=O] | (S)-3-(6-oxo-1,6-dihydropyridin-3-yl)-3-(2-oxo-3-(3-(5,6,7,8-tetrahydro-1,8-naphthyridin-2-yl)propyl)imidazolidin-1-yl)propanoic acid |
| A9R | 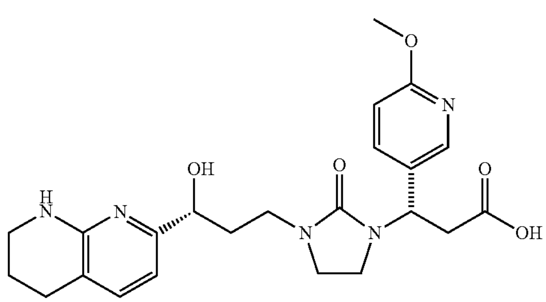 [SMILES: COc1ccc([C@H](CC(=O)O)N2CCN(CC[C@@H](O)c3ccc4c(n3)NCCC4)C2=O)cn1] | (S)-3-(3-((R)-3-hydroxy-3-(5,6,7,8-tetrahydro-1,8-naphthyridin-2-yl)propyl)-2-oxoimidazolidin-1-yl)-3-(6-methoxypyridin-3-yl)propanoic acid |
| A9S | 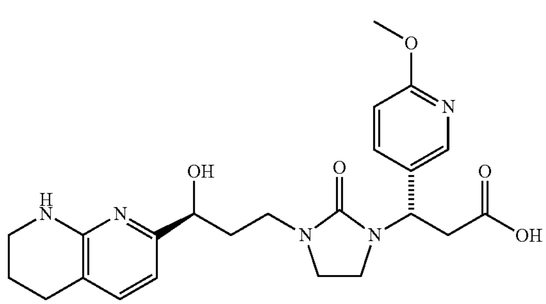 [SMILES: COc1ccc([C@H](CC(=O)O)N2CCN(CC[C@H](O)c3ccc4c(n3)NCCC4)C2=O)cn1] | (S)-3-(3-((S)-3-hydroxy-3-(5,6,7,8-tetrahydro-1,8-naphthyridin-2-yl)propyl)-2-oxoimidazolidin-1-yl)-3-(6-methoxypyridin-3-yl)propanoic acid |

| Cmpd # | Chemical Structure | Name |
| --- | --- | --- |
| A10E | 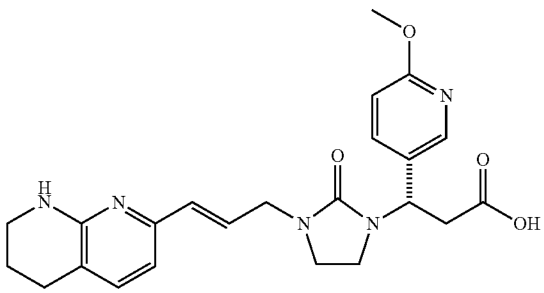 [SMILES: COc1ccc([C@H](CC(=O)O)N2CCN(C/C=C/c3ccc4c(n3)NCCC4)C2=O)cn1] | (S,E)-3-(6-methoxypyridin-3-yl)-3-(2-oxo-3-(3-(5,6,7,8-tetrahydro-1,8-naphthyridin-2-yl)-2-propenyl)imidazolidin-1-yl)propanoic acid |
| A10Z | 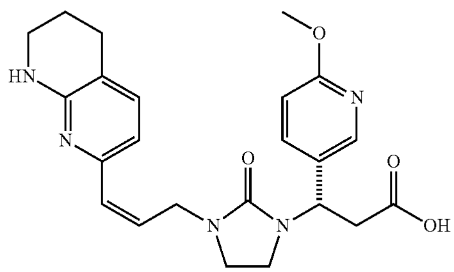 [SMILES: COc1ccc([C@H](CC(=O)O)N2CCN(C/C=C\c3ccc4c(n3)NCCC4)C2=O)cn1] | (S,Z)-3-(6-methoxypyridin-3-yl)-3-(2-oxo-3-(3-(5,6,7,8-tetrahydro-1,8-naphthyridin-2-yl)-2-propenyl)imidazolidin-1-yl)propanoic acid |
| A11 | 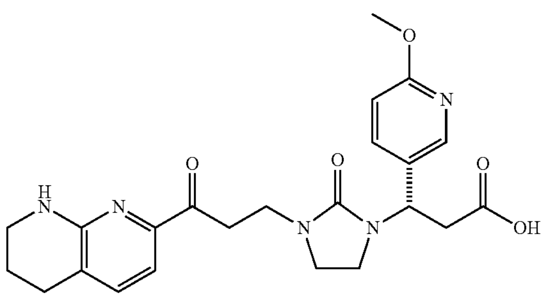 [SMILES: COc1ccc([C@H](CC(=O)O)N2CCN(CCC(=O)c3ccc4c(n3)NCCC4)C2=O)cn1] | (S)-3-(6-methoxypyridin-3-yl)-3-(2-oxo-3-(3-oxo-3-(5,6,7,8-tetrahydro-1,8-naphthyridin-2-yl)propyl)imidazolidin-1-yl)propanoic acid |

In one aspect, a compound of the present application inhibits the activity of one or more αv integrins (e.g., αvβ3, αvβ5, αvβ6, and αvβ8). In a further aspect, a compound of the present application inhibits the activity of αvβ3. In another further aspect, a compound of the present application inhibits the activity of αvβ5. In another further aspect, a compound of the present application inhibits the activity of αvβ6. In another further aspect, a compound of the present application inhibits the activity of αvβ8. In yet another further aspect, a compound of the present application inhibits the activity of αvβ3 and αvβ5. In yet another further aspect, a compound of the present application inhibits the activity of αvβ6 and αvβ8. In a further aspect, a compound of the present application inhibits the activity of αvβ3, αvβ5, αvβ6, and/or αvβ8 at a submicromolar concentration, e.g., below 1 µM, 0.8 µM, 0.6 µM, 0.5 µM, 0.2 µM, or 0.1 µM.

In one aspect, a compound of the present application inhibits cellular adhesion to vitronectin through the αv integrin (e.g., αvβ3 and αvβ5) at or below an IC$_{50}$ of 2.0E-07 M using a human dermal microvascular endothelial cell (HMVEC) assay. In one aspect, a compound of the present application inhibits cellular adhesion to vitronectin through the αv integrin (e.g., αvβ3 and αvβ5) at or below an IC$_{50}$ of 2.5E-07 M using a rat lung microvascular endothelial cell (RLMVEC) assay. In one aspect, a compound of the present application inhibits cellular adhesion to vitronectin through the αv integrin (e.g., αvβ3 and αvβ5) at or below an IC$_{50}$ of 2.0E-08 M using a rabbit aortic endothelial cell (RAEC) assay.

In one aspect, a compound of the present application inhibits cellular adhesion to fibronectin through the αv integrin (e.g., αvβ6 and αvβ8) at a micromolar concentration (e.g., at or below an IC$_{50}$ of 1.0E-05 M using a fibronectin binding assay).

In one aspect, a compound of the present application inhibits cellular adhesion to LAP-TGFβ1 (LAP1) through the αv integrin (e.g., αvβ6 and αvβ8) at a micromolar concentration (e.g., at or below an IC$_{50}$ of 1.0E-05 M using a LAP1 binding assay). In a further aspect, a compound of the present application inhibits cellular adhesion to LAP1 through the αv integrin (e.g., αvβ6 and αvβ8) at a submicromolar concentration (e.g., at or below an IC$_{50}$ of 1.0E-06 M using a LAP1 binding assay). In one aspect, a compound of the present application inhibits cellular adhesion to LAP1 through the αv integrin (e.g., αvβ6 and αvβ8) at a nanomolar concentration (e.g., at or below an IC$_{50}$ of 2.0E-08 M using a LAP1 binding assay). In a further aspect, a compound of the present application inhibits cellular adhesion to LAP1 through the αv integrin (e.g., αvβ6 and αvβ8) at a subnanomolar concentration (e.g., at or below an IC$_{50}$ of 1.0E-08 M using a LAP1 binding assay).

In one aspect, the compounds of the present application are selective for one αv integrin (e.g., αvβ3, αvβ5, αvβ6, or αvβ8) over other αv integrins (e.g., αvβ3, αvβ5, αvβ6, or αvβ8). As used herein, "selective" means that a compound, for example a compound of the application, inhibits one αv integrin to a greater extent than other αv integrins.

A "selective αv integrin inhibitor" can be identified, for example, by comparing the ability of a compound to inhibit one αv integrin activity to its ability to inhibit other αv integrins. For example, a compound may be assayed for its ability to inhibit αvβ6 activity, as well as αvβ3, αvβ5, and αvβ8 or other αv integrins.

In certain embodiments, the compounds of the application exhibit at least 1.2-fold, 1.5-fold, 2-fold, 3-fold, 5-fold, 10-fold, 25-fold, 50-fold or 100-fold selectivity for one αv integrin over other αv integrins (e.g., as measured by $IC_{50}$). In various embodiments, the compounds of the application exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for one αv integrin over other αv integrins. In various embodiments, the compounds of the application exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for one αv integrin over other αv integrins. In various embodiments, the compounds of the application exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for one αv integrin over other αv integrins.

In one embodiment, the compounds of the application exhibit at least 1.2-fold, 1.5-fold, 2-fold, 3-fold, 5-fold, 10-fold, 25-fold, 50-fold or 100-fold selectivity for αvβ3 over the αvβ5, αvβ6, and/or αvβ8 integrin (e.g., as measured by $IC_{50}$). In various embodiments, the compounds of the application exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for αvβ3 over the αvβ5, αvβ6, and/or αvβ8 integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for αvβ3 over the αvβ5, αvβ6, and/or αvβ8 integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for αvβ3 over the αvβ5, αvβ6, and/or αvβ8 integrin.

In another embodiment, the compounds of the application exhibit at least 1.2-fold, 1.5-fold, 2-fold, 3-fold, 5-fold, 10-fold, 25-fold, 50-fold or 100-fold selectivity for αvβ5 over the αvβ3, αvβ6, and/or αvβ8 integrin (e.g., as measured by $IC_{50}$). In various embodiments, the compounds of the application exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for αvβ5 over the αvβ3, αvβ6, and/or αvβ8 integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for αvβ5 over the αvβ3, αvβ6, and/or αvβ8 integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for αvβ5 over the αvβ3, αvβ6, and/or αvβ8 integrin.

In another embodiment, the compounds of the application exhibit at least 1.2-fold, 1.5-fold, 2-fold, 3-fold, 5-fold, 10-fold, 25-fold, 50-fold or 100-fold selectivity for αvβ6 over the αvβ3, αvβ5, and/or αvβ8 integrin (e.g., as measured by $IC_{50}$). In various embodiments, the compounds of the application exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for αvβ6 over the αvβ3, αvβ5, and/or αvβ8 integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for αvβ6 over the αvβ3, αvβ5, and/or αvβ8 integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for αvβ6 over the αvβ3, αvβ5, and/or αvβ8 integrin.

In another embodiment, the compounds of the application exhibit at least 1.2-fold, 1.5-fold, 2-fold, 3-fold, 5-fold, 10-fold, 25-fold, 50-fold or 100-fold selectivity for αvβ6 over the αvβ8 integrin (e.g., as measured by $IC_{50}$). In various embodiments, the compounds of the application exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for αvβ6 over the αvβ8 integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for αvβ6 over the αvβ8 integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for αvβ6 over the αvβ8 integrin.

In another embodiment, the compounds of the application exhibit at least 1.2-fold, 1.5-fold, 2-fold, 3-fold, 5-fold, 10-fold, 25-fold, 50-fold or 100-fold selectivity for αvβ8 over the αvβ3, αvβ5, and/or αvβ6 integrin (e.g., as measured by $IC_{50}$). In various embodiments, the compounds of the application exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for αvβ8 over the αvβ3, αvβ5, and/or αvβ6 integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for αvβ8 over the αvβ3, αvβ5, and/or αvβ6 integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for αvβ8 over the αvβ3, αvβ5, and/or αvβ6 integrin.

In another embodiment, the compounds of the application exhibit at least 1.2-fold, 1.5-fold, 2-fold, 3-fold, 5-fold, 10-fold, 25-fold, 50-fold or 100-fold selectivity for αvβ8 over the αvβ6 integrin (e.g., as measured by $IC_{50}$). In various embodiments, the compounds of the application exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for αvβ8 over the αvβ6 integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for αvβ8 over the αvβ6 integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for αvβ8 over the αvβ6 integrin.

In another embodiment, the compounds of the application exhibit at least 1.2-fold, 1.5-fold, 2-fold, 3-fold, 5-fold, 10-fold, 25-fold, 50-fold or 100-fold selectivity for each of αvβ6 and αvβ8 over the αvβ3 and/or αvβ5 integrin (e.g., as measured by $IC_{50}$). In various embodiments, the compounds of the application exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for each of αvβ6 and αvβ8 over the αvβ3 and/or αvβ5 integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for each of αvβ6 and αvβ8 over the αvβ3 and/or αvβ5 integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for each of αvβ6 and αvβ8 over the αvβ3 and/or αvβ5 integrin.

In another embodiment, the compounds of the application exhibit at least 1.2-fold, 1.5-fold, 2-fold, 3-fold, 5-fold, 10-fold, 25-fold, 50-fold or 100-fold selectivity for each of αvβ3 and αvβ5 over the αvβ6 and/or αvβ8 integrin (e.g., as measured by $IC_{50}$). In various embodiments, the compounds of the application exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for each of αvβ3 and αvβ5 over the αvβ6 and/or αvβ8 integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for each of αvβ3 and αvβ5 over the αvβ6 and/or αvβ8 integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for each of αvβ3 and αvβ5 over the αvβ6 and/or αvβ8 integrin.

In another embodiment, the compounds of the application exhibit at least 1.2-fold, 1.5-fold, 2-fold, 3-fold, 5-fold, 10-fold, 25-fold, 50-fold or 100-fold selectivity for each of αvβ5 and αvβ6 over the αvβ3 and/or αvβ8 integrin (e.g., as measured by $IC_{50}$). In various embodiments, the compounds of the application exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for each of $\alpha v \beta 5$ and $\alpha v \beta 6$ over the $\alpha v \beta 3$ and/or $\alpha v \beta 8$ integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for each of $\alpha v \beta 5$ and $\alpha v \beta 6$ over the $\alpha v \beta 3$ and/or $\alpha v \beta 8$ integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for each of $\alpha v \beta 5$ and $\alpha v \beta 6$ over the $\alpha v \beta 3$ and/or $\alpha v \beta 8$ integrin.

In another embodiment, the compounds of the application exhibit at least 1.2-fold, 1.5-fold, 2-fold, 3-fold, 5-fold, 10-fold, 25-fold, 50-fold or 100-fold selectivity for each of $\alpha v \beta 3$ and $\alpha v \beta 6$ over the $\alpha v \beta 5$ and/or $\alpha v \beta 8$ integrin (e.g., as measured by $IC_{50}$). In various embodiments, the compounds of the application exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for each of $\alpha v \beta 3$ and $\alpha v \beta 6$ over the $\alpha v \beta 5$ and/or $\alpha v \beta 8$ integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for each of $\alpha v \beta 3$ and $\alpha v \beta 6$ over the $\alpha v \beta 5$ and/or $\alpha v \beta 8$ integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for each of $\alpha v \beta 3$ and $\alpha v \beta 6$ over the $\alpha v \beta 5$ and/or $\alpha v \beta 8$ integrin.

In another embodiment, the compounds of the application exhibit at least 1.2-fold, 1.5-fold, 2-fold, 3-fold, 5-fold, 10-fold, 25-fold, 50-fold or 100-fold selectivity for each of $\alpha v \beta 3$ and $\alpha v \beta 8$ over the $\alpha v \beta 5$ and/or $\alpha v \beta 6$ integrin (e.g., as measured by $IC_{50}$). In various embodiments, the compounds of the application exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for each of $\alpha v \beta 3$ and $\alpha v \beta 8$ over the $\alpha v \beta 5$ and/or $\alpha v \beta 6$ integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for each of $\alpha v \beta 3$ and $\alpha v \beta 8$ over the $\alpha v \beta 5$ and/or $\alpha v \beta 6$ integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for each of $\alpha v \beta 3$ and $\alpha v \beta 8$ over the $\alpha v \beta 5$ and/or $\alpha v \beta 6$ integrin.

In another embodiment, the compounds of the application exhibit at least 1.2-fold, 1.5-fold, 2-fold, 3-fold, 5-fold, 10-fold, 25-fold, 50-fold or 100-fold selectivity for each of $\alpha v \beta 5$ and $\alpha v \beta 8$ over the $\alpha v \beta 3$ and/or $\alpha v \beta 6$ integrin (e.g., as measured by $IC_{50}$). In various embodiments, the compounds of the application exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for each of $\alpha v \beta 5$ and $\alpha v \beta 8$ over the $\alpha v \beta 3$ and/or $\alpha v \beta 6$ integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for each of $\alpha v \beta 5$ and $\alpha v \beta 8$ over the $\alpha v \beta 3$ and/or $\alpha v \beta 6$ integrin. In various embodiments, the compounds of the application exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for each of $\alpha v \beta 5$ and $\alpha v \beta 8$ over the $\alpha v \beta 3$ and/or $\alpha v \beta 6$ integrin.

In one aspect, a compound of the present application inhibits or decreases formation of fibrotic tissue in an organ (e.g., kidney, lung, liver, and heart). In one aspect, a compound of the present application decreases the formation of fibrotic tissue below 90%, 80%, 70%, 60%, 50%, 40%, 30%, 20%, 10%, or 5%, as compared to that in an untreated control. In a further aspect, a compound of the present application decreases the formation of fibrotic tissue below 60%, 50%, 40%, 30%, 20%, 10%, or 5%, as compared to that in an untreated control. In a further aspect, a compound of the present application decreases the formation of fibrotic tissue below 40%, 30%, 20%, 10%, or 5%, as compared to that in an untreated control.

Compounds of the present application can be conveniently prepared by a variety of methods familiar to those skilled in the art (e.g., according to the methods described in U.S. Pat. No. 6,017,926, the entire contents of which are incorporated by reference). The compounds of each of the formulae described herein may be prepared from commercially available starting materials or starting materials which can be prepared using literature procedures.

The compounds of the application may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers. It is intended that all of the possible optical isomers and diastereomers in mixtures and as pure or partially purified compounds are included within the ambit of the application. The application is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

In the present specification, the structural formula of the compound represents a certain isomer for convenience in some cases, but the present application includes all isomers, such as geometrical isomers, optical isomers based on an asymmetrical carbon, stereoisomers, tautomers, and the like.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule of Cahn*, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. In one example,

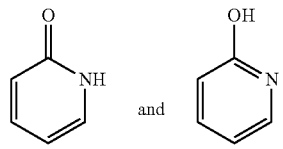 [SMILES: O=c1cccc[nH]1 ; Oc1ccccn1]

are tautomers to each other.

It is to be understood that the compounds of the present application may be depicted as different tautomers. It should also be understood that when compounds have tautomeric forms, all tautomeric forms are intended to be included in the scope of the present application, and the naming of the compounds does not exclude any tautomer form.

If desired, racemic mixtures of the compounds may be separated so that the individual enantiomers are isolated. The separation can be carried out by methods well known in the art, such as contacting a racemic mixture of compounds with an enantiomerically pure compound to form a diastereomeric mixture, followed by separation of the individual diastereomers by standard methods, such as fractional crystallization or chromatography. The diastereomeric mixture is often a mixture of diasteriomeric salts formed by contacting a racemic mixture of compounds with an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which are well known in the art.

Alternatively, any enantiomer of a compound may be obtained by stereoselective synthesis using optically pure starting materials or reagents of known configuration by methods well known in the art.

Some of the compounds of the application may exist in unsolvated as well as solvated forms such as, for example, hydrates.

"Solvate" means a solvent addition form that contains either a stoichiometric or non-stoichiometric amounts of the solvent molecules. Some compounds have a tendency to trap a fixed molar ratio of the solvent molecules in the crystalline solid state, thus forming a solvate. If the solvent is water, the solvate formed is a hydrate. When the solvent is alcohol, the solvate formed is an alcoholate. Hydrates are formed by the combination of one or more molecules of water with one of the substances (e.g., a compound of the application) in which the water retains its molecular state as H₂O, such combination being able to form one or more hydrate. In hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates include sesquihydrates, monohydrates, dehydrates, and trihydrates. Equally suitable are the hydrates of salts of the compounds of the application.

For use in medicine, the salts of the compounds of the application refer to non-toxic "pharmaceutically acceptable salts". Other salts may, however, be useful in the preparation of the compounds of the application or pharmaceutically acceptable salts thereof. Salts encompassed within the term "pharmaceutically acceptable salts" refer to non-toxic salts of the compounds of the application which can be prepared by reacting the free base with a suitable organic or inorganic acid. Representative salts include the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamottle (embonate), palmitate, pantothenate, phosphate/diphosphate, polygalacturonate, salicylate, stearate, sulfate, subacetate, succinate, tannate, tartrate, teoclate, tosylate, triethiodide, and valerate. Furthermore, where the compounds of the application carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts which may be derived from ammonia or organic amines, such as, for example, diethylamine, triethylamine, ethyldiisopropylamine, procaine, dibenzylamine, N-methylmorpholine, dihydroabietylamine, or methylpiperidine.

The application includes within its scope prodrugs of the compounds of the application. In general, such prodrugs will be functional derivatives of the compounds of the application which are readily convertible in vivo into the required compound. Thus, in the methods of treatment of the application, the term "administering" shall encompass the treatment of the various disease and conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of the application into the biological milieu.

The application also includes one or more metabolites of a compound of the application.

The present application also comprehends deuterium labeled compounds of each of the formulae described herein or the compounds listed in Table 1, wherein a hydrogen atom is replaced by a deuterium atom. The deuterium labeled compounds comprise a deuterium atom having an abundance of deuterium that is substantially greater than the natural abundance of deuterium, e.g., 0.015%.

The term "deuterium enrichment factor" as used herein means the ratio between the deuterium abundance and the natural abundance of a deuterium. In one aspect, a compound of the application has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (990.5% deuterium incorporation).

Deuterium labeled compounds can be prepared using any of a variety of art-recognized techniques. For example, deuterium labeled compounds of each of the formulae described herein or the compounds listed in Table 1 can generally be prepared by carrying out the procedures described herein, by substituting a readily available deuterium labeled reagent for a non-deuterium labeled reagent.

A compound of the application or a pharmaceutically acceptable salt or solvate thereof that contains the aforementioned deuterium atom(s) is within the scope of the application. Further, substitution with deuterium, i.e., $^2H$, can afford certain therapeutic advantages resulting from greater metabolic stability, for example, increased in vivo half-life and/or reduced dosage requirements.

Biological Assays
Cell Adhesion Assays

The ability of compounds of the application to block cell adhesion to vitronectin and/or fibronectin may be tested with methods or techniques known in the art, for example, the procedure described below.

Adhesion plates preparation: Cell culture plates are coated with vitronectin or fibronectin.

Cell culturing and loading: Exemplary cells (e.g., HMVEC cells, RLMVEC cells, and RAEC cells) are used for the compound testing. Cells are grown and then suspended for testing.

Adhesion assay: Test compounds are added to the cell suspension. After incubation, the cells that do not adhere to vitronectin- or fibronectin-coated plates are removed by gentle washing. The number of the remaining cells is measured. IC$_{50}$ values are calculated.

αVβ6/αVβ8—LAP-TGF β1 Binding Assay

Integrins αVβ6/αVβ8 coupled beads are treated with an αVβ6/αVβ8 ligand (e.g., LAP TGF-β1 (LAP1)), and the complex is incubated with a primary antibody (Ab), which can be labeled for detection (e.g., fluorescently labeled), and optionally with a secondary antibody, which can be labeled for detection (e.g., fluorescently labeled). Reaction between integrin coupled beads and the ligand was considered as the full reaction, and reaction without the ligand or a compound of the disclosure was considered as the blank reaction. The complex is analyzed, e.g., by either plate reader or Flow Cytometer, to determine modulation of binding between αVβ6/αVβ8 and the ligand (e.g., LAP-TGF Pβ1) by the compounds of the present application.

αVβ3/αVβ5—LAP-TGF/3 Binding assay

Integrins αVβ3/αVβ5 coupled beads are treated with an αVβ3/αVβ5 ligand (e.g., vitronectin), and the complex is treated with a primary antibody (Ab), which can be labeled for detection (e.g., fluorescently labeled), and optionally with a secondary antibody, which can be labeled for detection (e.g., fluorescently labeled). Reaction between integrin coupled beads and the ligand was considered as the full reaction, and reaction without the ligand or a compound of the disclosure was considered as the blank reaction. The complex is analyzed, e.g., by either plate reader or Flow Cytometer, to determine modulation of binding between $\alpha V\beta 3/\alpha V\beta 5$ and the ligand (e.g., vitronectin) by the compounds of the present application.

Anti-angiogenic Activity Assay

The anti-angiogenic ability of compounds of the application may be tested with methods or techniques known in the art, for example, the procedure described below.

Chick chorioallantoic membrane (CAM) is grafted with gelatin sponges impregnated with the test compounds and VEGF. Untreated CAM received only VEGF.

Albumin is removed from hen eggs and incubated. Grafts are placed on developing CAMs and further incubated. CAMs are then fixed, dissected and imaged for blood vessel growth.

Distribution in plasma of the compounds of the application, and the in vivo safety and efficacy of the compounds of the application may be tested using animals after administration of the compounds to the animals.

Fibrosis can be generally recognized based on the distinct morphology of fibrous tissue in a biopsy of the organ in which fibrosis is suspected. Other means for detecting the presence of fibrosis or developing fibrosis include computerized axial tomography (CAT or CT) scan, ultrasound, magnetic resonance imaging (MRI), and monitoring the level of one or more serum markers known to be indicative of fibrosis (e.g., various types of collagens). The precise manner of diagnosing fibrosis also varies depending on the organ where the fibrotic process takes place. For instance, biopsies are generally effective for diagnosing fibrosis of most organs, whereas endoscopy involving a fiber optic instrument (e.g., a sigmoidoscope or a colonoscope) can be a less traumatic alternative to detect fibrosis of certain organs such as the intestine.

Biopsy for Detecting Fibrosis

Procedures for obtaining biopsy from a given organ or tissue are known, e.g., through exploratory surgery, or a biopsy needle. Upon obtaining a biopsy, the sample is examined and given a score to indicate the presence and level of fibrosis in the sample. Frequently used scoring systems include: the METAVIR scoring system, modified HAI (ISHAK) scoring system, and the Knodell scoring system. The criteria used in scoring are well established and known to those of skilled in the art.

Fibrosis Markers

There are numerous known serum markers whose level can be indicative of the presence and/or severity of fibrosis, including hyaluronic acid, laminin, undulin (type IV collagen) pro-peptides from types I, II, and IV collagens, lysyl oxidase, prolyl hydroxylase, lysyl hydroxylase, PIIINP, PICP, collagen VI, tenascin, collagen XIV, laminin P1, TIMP-1, MMP-2, $\alpha 2$ macroglobulin, haptoglobin, gamma glutamyl transpeptidase, $\gamma$ globulin, total bilirubin, and apolipoprotein A1.

Animal Fibrosis Models

The anti-fibrotic activities of the compounds of the present application can be assessed in various animal models for evaluating fibrosis, including lung fibrosis and liver fibrosis. Animal models for studying fibrosis are known (see, e.g., Henderson et al., *Nat Med* 19, 617 (2013), Pilling et al., *J. Immunol.* 179, 4035 (2007), Truong et al., *Biomed. Res. Ther.* 1, 43 (2014)). For example, animals (e.g., rats, mice, rabbits, monkeys) can be treated with various lung fibrosis inducing agents (e.g., bleomycin). Compounds of the present application are then administered to the animals at various doses. The effect of the compounds can be evaluated by measuring expression of fibrosis marker genes or collagen formation in the lung tissues, or by immunohistochemistry. In other examples, animals (e.g., rats, mice, rabbits, monkeys) can be treated to induce liver fibrosis (e.g., by chemical agents such as $CCl_4$, or through bile duct ligation). Compounds of the present application are then administered to the animals at various doses, liver histopathology, and connective tissue formation.

In vivo Bleomycin Induced Pulmonary Fibrosis Model.

Experimental animals are randomly and prospectively assigned to groups. On day 0 and prior to bleomycin induction, animals are administered the first dose of vehicle or a compound of the present disclosure. Following dosing, all animals are anesthetized. A small diameter cannula is inserted into the trachea and saline or bleomycin is slowly infused into the lungs. Group 1 serves as an untreated control group and receives saline only (no bleomycin) on day 0. The other groups receive bleomycin on day 0. Treatments with vehicle (e.g., methylcellulose), positive control (e.g., Pirfenidone), or a compound of the present disclosure are administered once or twice daily via oral gavage (PO). All animals are weighed and evaluated daily for respiratory distress.

Prior to sacrifice, animals are anesthetized and once the animal is determined to be non-responsive a shallow incision is made. The trachea is isolated and a transverse cut is made between tracheal rings approximately half-way through the trachea. A tracheotomy is performed by the insertion of a cannula through the incision secured with surgical suture to the trachea. Following cannulation, the adapter end of the cannula is attached to the mechanical ventilator. The animal is ventilated and following an acclimation period, lung volume is standardized and each animal undergoes a measure of total respiratory impedance.

Pharmaceutical Compositions

The present application relates to pharmaceutical compositions comprising a compound of the application as an active ingredient. In one aspect, the application provides a pharmaceutical composition comprising at least one compound of each of the formulae described herein, or a pharmaceutically acceptable salt or solvate thereof and one or more pharmaceutically acceptable carriers or excipients. In one aspect, the application provides a pharmaceutical composition comprising at least one compound selected from Table 1.

As used herein, the term "composition" is intended to encompass a product comprising the specified ingredients in the specified amounts, as well as any product which results, directly or indirectly, from combination of the specified ingredients in the specified amounts.

The compounds of the application can be formulated for oral administration in forms such as tablets, capsules (each of which includes sustained release or timed release formulations), pills, powders, granules, elixirs, tinctures, suspensions, syrups and emulsions. The compounds of the application can also be formulated for intravenous (bolus or in-fusion), intraperitoneal, topical, subcutaneous, intramuscular or transdermal (e.g., patch) administration, all using forms well known to those of ordinary skill in the pharmaceutical arts.

For topical administration, the compositions are provided as a formulation comprising a compound of the present application in concentration between about 0.01 and about 5 weight percent, preferably between about 0.1 and about 5.0 weight percent, more preferably between about 0.5 and about 5.0 weight percent, and most preferably between about 0.8 and about 3.0 weight percent.

The topic formulation of the present application may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulphated β-cyclodextrin (S-β-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof. Preferably, solubility enhancing agent includes β-cyclodextrin sulfobutyl ether, hyrdoxypropyl-β-cyclodextrin, sulphated β-cyclodextrin (S-β-CD), and maltosyl-β-cyclodextrin, and mixtures thereof. β-cyclodextrin sulfobutyl ether is a particularly preferred solubility enhancing agent. The solubility enhancing agent(s) may be added in an amount of about 1 to about 20 wt %, preferably about 1 to about 10 wt %, and more preferably about 5 to about 10 wt %.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof. Disodium edetate is a particularly preferred chelating agent. The chelating agent(s) may be added in an amount of about 0.001 to about 0.05 wt %, preferably about 0.001 to about 0.02 wt %, more preferably about 0.002 to about 0.01 wt %, and most preferably about 0.002 to about 0.005 wt %.

Preferably, the aqueous vehicle includes a preservative. Preferred preservatives include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, sorbic acid, and mixtures thereof. More preferably, the preservative is a quaternary ammonium salt such as benzalkonium halides (preferably benzalkonium chloride), chlorhexidine gluconate, benzethonium chloride, cetyl pyridinium chloride, potassium sorbate, sodium benzoate, ethyl p-hydroxybenzoate, butyl p-hydroxybenzoate, or propylaminopropyl biguanide, or mixtures thereof. Propylaminopropyl biguanide is an especially preferred preservative. The preservative(s) may be used in an amount of about 0.00001 to about 0.0001 wt %, preferably about 0.00001 to about 0.00008 wt %, and more preferably about 0.00002 to about 0.00005 wt %.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof. Preferably, the tonicity agent is selected from the group consisting of glycerin, mannitol, potassium chloride, and sodium chloride. More preferably mannitol and/or sodium chloride (and most preferably a mixture thereof) are employed. The tonicity agent(s) may be used in an amount of about 0.05 to about 8 wt %, preferably about 0.1 to about 6 wt %, more preferably about 0.1 to about 4 wt %, and most preferably about 0.2 to about 4 wt %.

The aqueous vehicle may also contains a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof. In preferred embodiments of the present application, the viscosity/suspending agent is a carbomer, more preferably Carbopol 974P. The viscosity/suspending agent(s) may be present in an amount of about 0.05 to about 2 wt %, preferably 0.1 to about 1 wt %, more preferably about 0.2 to about 0.8 wt %, and most preferably about 0.3 to about 0.5 wt %.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilize the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ε-aminocaproic acid, and mixtures thereof. The buffer agent(s) may be present in an amount of about 0.05 to about 5 wt %, preferably 0.1 to about 5 wt %, more preferably about 0.2 to about 5 wt %, and most preferably about 0.5 to about 5 wt %.

The formulation for topical administration may further comprise a wetting agent. In any embodiment of the present application the wetting agent is preferably a non-ionic wetting agent. More preferably, the wetting agent is water soluble or swellable. Most preferably the wetting agent is water soluble. "Water soluble" is to be understood in the manner used in standard texts such as the "Handbook of Pharmaceutical Excipients" (Raymond C Rowe, Paul J Sheskey and Sian C Owen, Fifth Edition, Pharmaceutical Press and American Pharmacists Association 2006). Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Specific examples of suitable wetting agents include those selected from the group consisting of: polyoxyethylene-polyoxypropylene block copolymers (poloxamers) such as: polyoxyethylene (160) polyoxypropylene (30) glycol [Pluronic F68], polyoxyethylene (42) polyoxypropylene (67) glycol [Pluronic P123], polyoxyethylene (54) polyoxypropylene (39) glycol [Pluronic P85], polyoxyethylene (196) polyoxypropylene (67) glycol [Poloxamer 407, Pluronic F127], polyoxyethylene (20) polyoxypropylene (20) glycol [Pluronic L44], polyoxyethylenated sorbitan esters (polysorbates) such as poly(oxyethylene)sorbitan monopalmitate (polysorbate 40), poly(oxyethylene)sorbitan monostearate (polysorbate 60), poly(oxyethylene)sorbitan tristearate (polysorbate 65), poly(oxyethylene) sorbitan monooleate (polysorbate 80), poly(oxyethylene) sorbitan monolaurate, poly(oxyethylene) sorbitan trioleate, polyethoxylated ethers of castor oils such as polyoxyethylene hydrogenated castor oil 10, polyoxyethylene hydrogenated castor oil 40, polyoxyethylene hydrogenated castor oil 50 and polyoxyethylene liydrogenated castor oil 60, polyoxyl 40 stearate, sucrose fatty esters, and polyoxyethylene fatty esters, and mixtures thereof.

Particularly preferred formulations for topical administration of the present application comprise a compound of the present application, a solubility enhancing agent, a cheating agent, a preservative, a tonicity agent, a viscosity/suspending agent, a buffer, and a pH modifying agent. More particularly preferred formulations are comprised of an aqueous solution of a 3-cyclodextrin, a borate salt, boric acid, sodium chloride, disodium edetate, and propylaminopropyl biguanide.

In one aspect, the formulation of the present application is in the form of a solution, such as one of the following:

| Solution Composition | |
| --- | --- |
| a compound of the application | 0.1-5.0 g |
| a solubility enhancing agent | 1-20 g |
| a buffering agent | 0.05-5.0 g |
| an tonicity agent | 0.05-8 g |
| a chelating agent | 1-50 mg |
| a preservative | 0.01-0.1 mg |
| water | 100 ml |

| Solution Composition | |
| --- | --- |
| a compound of the application | 0.8-3.0 g |
| a solubility enhancing agent | 5-10 g |
| a buffering agent | 0.5-5.0 g |
| an tonicity agent | 0.2-4 g |
| a chelating agent | 2-5 mg |
| a preservative | 0.02-0.05 mg |
| water | 100 ml |

| Solution Composition | I | II | III | IV |
| --- | --- | --- | --- | --- |
| a compound of the application | 2.5 g | 2.0 g | 1.5 g | 1.0 g |
| a solubility enhancing agent | 10 g | 10 g | 10 g | 5 g |
| buffering agent 1 | 1.05 g | 1.05 g | 1.05 g | 1.05 g |
| buffering agent 2 | 0.285 g | 0.285 g | 0.285 g | 0.285 g |
| an tonicity agent | 0.25 g | 0.25 g | 0.25 g | 0.25 g |
| a chelating agent | 2.5 mg | 2.5 mg | 2.5 mg | 2.5 mg |
| a preservative | 0.03 mg | 0.03 mg | 0.03 mg | 0.03 mg |
| water | 100 ml | 100 ml | 100 ml | 100 ml |

The topic formulation of the present application may also be in the form of a gel or a semi-gel, or both; a jelly; a suspension; an emulsion; an oil; an ointment; a cream; or a spray.

The gel, semi-gel, jelly, suspension, emulsion, oil, ointment, cream, or spray may contain various additives incorporated ordinarily, such as buffering agents (e.g., phosphate buffers, borate buffers, citrate buffers, tartrate buffers, acetate buffers, amino acids, sodium acetate, sodium citrate and the like), tonicity agents (e.g., saccharides such as sorbitol, glucose and mannitol, polyhydric alcohols such as glycerin, concentrated glycerin, PEG and propylene glycol, salts such as sodium chloride), preservatives or antiseptics (e.g., benzalkonium chloride, benzalkonium chloride, P-oxybenzoates such as methyl p-oxybenzoate or ethyl p-oxybenzoate, benzyl alcohol, phenethyl alcohol, sorbic acid or its salt, thimerosal, chlorobutanol and the like), solubilizing enhancing agents (e.g., cyclodextrins and their derivative, water-soluble polymers such as polyvinyl pyrrolidone, surfactants such as tyloxapol, polysorbates), pH modifiers (e.g., hydrochloric acid, acetic acid, phosphoric acid, sodium hydroxide, potassium hydroxide, ammonium hydroxide and the like), thickening agents (e.g., HEC, hydroxypropyl cellulose, methyl cellulose, HPMC, carboxymethyl cellulose and their salts), chelating agents (e.g., sodium edetate, sodium citrate, condensed sodium phosphate) and the like.

Furthermore the compounds of the application may be formulated for topical administration by incorporation into novel formulations including but not limited to: microemulsions, liposomes, niosomes, gels, hydrogel, nanoparticles, and nanosuspension.

1. Microemulsions

Microemulsions are dispersion of water and oil facilitated by a combination of surfactant and cosurfactant in a manner to reduce interfacial tension. These systems are usually characterized by higher thermodynamic stability, small droplet size (approximately 100 nm) and clear appearance. Their transparent appearance is due to the high level of dispersion of the internal phase, and the size of it ranges from 100-1000 angstroms.

2. Liposomes

Liposomes are lipid vesicles containing aqueous core and have been widely exploited in delivery for various drug substances. Depending on the nature of the lipid composition selected, liposomes can provide extended release of the drug.

3. Niosomes

Niosomes are bilayered structural vesicles made up of nonionic surfactant and are capable of encapsulating both lipophilic and hydrophilic compounds. They can release the drug independent of pH and enhance bioavailability. Niosomes are microscopic lamellar structures that are formed on the admixture of nonionic surfactant of the alkyl or diakyl polyglycerol ether class and cholesterol with subsequent hydration in aqueous media. Structurally niosomes are similar to liposomes, in that they are also made up of a bilayer. However, the bilayer in the case of nisomes is made up of nonionic surface-active agents rather than phospholipids as in the case of liposomes. Niosomes may be unilamellar or multilamellar depending on the method used to prepare them. They are capable of entrapping hydrophilic and hydrophobic solutes. They possess great stability and lack many disadvantages associate with liposomes such as high cost and the variable purity of phospholipids. The properties of niosomes and process for preparing them are well known in the art, see e.g., Wagh V D et al., *J Pharm Res* 2010; 3(7):1558-1563; Kaur H et al., *IntJPharm Sci Rev Res* 2012; 15(1): 113-120, each of which is incorporated by reference.

4. Gels

Gels are composed of mucoadhesive polymers that provide localized delivery of an active ingredient. Such polymers have a property known as bioadhesion, meaning attachment of a drug carrier to a specific biological tissue. These polymers are able to extend the contact time of the drug with the biological tissues and thereby improve bioavailability. The choice of the polymer plays a critical role in the release kinetics of the drug from the dosage form. Several bioadhesive polymers are available with varying degree of mucoadhesive performance. Some examples are carboxymethylcellulose, carbopol, polycarbophil, and sodium alginate.

5. Hydrogels

Hydrogels are three-dimensional, hydrophilic, polymeric networks capable of taking in large amounts of water or biological fluids. Residence time can be significantly enhanced with a hydrogel formulation. The gelation can be obtained by changing temperature and pH. Poloxamers, the most widely used polymer, contains the hydrophobic part in the centre surrounded by a hydrophilic part.

6. Nanoparticles

Nanoparticles are defined as particles with a diameter of less than 1 μm, comprising of various biodegradable or non biodegradable polymers, lipids, phospholipids or metals. They can be classified as nanospheres or nanocapsules depending upon whether the drug has been uniformly dispersed or coated within polymeric material. The uptake and distribution of nanoparticles is dependent on their size.

7. Nanosuspensions

Nanosuspensions are defined as sub-micron colloidal systems that consist of poorly water soluble drugs suspended in an appropriate dispersion medium stabilized by surfactants. Usually, nanosuspensions consist of colloidal carriers like polymeric resins which are inert in nature. Nanosuspensions enhance drug solubility and thus bioavailability. Unlike microemulsions, nanosuspensions are non-irritant. Charge on the surface of nanoparticles facilitates their adhesion to the cornea. The use of nanosuspensions in drug delivery is reviewed in Rabinow, *Nature Rev Drug Disc* 2004; 785-796, which is incorporated by reference.

The compounds of the application may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, and polyethyleneoxide-polylysine substituted with palmitoyl residues. Furthermore, the compounds of the application may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The present application also provides a pharmaceutical composition comprising a compound of the application or a pharmaceutically acceptable salt or solvate thereof, and a pharmaceutically acceptable carrier or excipient, and further an active ingredient selected from the group consisting of a) an antagonist of integrin α5β1, b) a cytotoxic/antiproliferative agent, c) an inhibitor of epidermal-derived, fibroblast-derived, or platelet-derived growth factor, d) an inhibitor of VEGF, e) an inhibitor of Flk-1/KDR, Flt-1, Tck/Tie-2, or Tic-1, and f) an inhibitor of phosphoinositide 3-kinase, and a mixture thereof.

The present application further provides a pharmaceutical composition comprising a compound of the application or a pharmaceutically acceptable salt or solvate thereof, and a pharmaceutically acceptable carrier or excipient, and further an active ingredient selected from the group consisting of a) an antagonist of integrin α5β1, b) a cytotoxic/antiproliferative agent, c) an inhibitor of epidermal-derived, fibroblast-derived, or platelet-derived growth factors, d) an inhibitor of VEGF, and e) an inhibitor of phosphoinositide 3-kinase, and a mixture thereof.

Nonlimiting examples of antagonists of integrin α5β1 are (S)-2-((R)-2-((S)-2-((S)-2-((S)-1-acetylpyrrolidine-2-carboxamido)-3-(1H-imidazol-5-yl)propanamido)-3-hydroxypropanamido)-3-mercaptopropanamido)succinamide, and JSM6427, described in Stragies, R. et al., *J. Med. Chem.* 2007, 50:3786-3794, herein incorporated by reference.

Nonlimiting examples of cytotoxic/antiproliferative agents are taxol, vincristine, vinblastine, and doxorubicin.

Nonlimiting examples of inhibitors of epidermal-derived, fibroblast-derived, or platelet-derived growth factors are pazopanib, and sunitinib, Nonlimiting examples of inhibitors of vascular endothelial derived growth factor (VEGF) are bevacizumab and ranibizumab, Nonlimiting examples of inhibitors of phosphoinositide 3-kinase are indelalisib and 2-morpholin-4-yl-8-phenylchroman-4-one.

Methods of Use

"Fibrosis" refers to a condition involving the development of excessive fibrous connective tissue, e.g., scar tissue, in a tissue or organ. Such generation of scar tissue may occur in response to infection, inflammation, or injury of the organ due to a disease, trauma, chemical toxicity, and so on. Fibrosis may develop in a variety of different tissues and organs, including the liver, kidney, intestine, lung, heart, etc.

Fibrosis of organs or tissues is involved in various diseases or disorders, such as (1) renal diseases (e.g., tubulointerstitial nephritis), (2) respiratory diseases (e.g., interstitial pneumonia (pulmonary fibrosis)), (3) gastrointestinal diseases (e.g., hepatocirrhosis, chronic pancreatitis and scirrhous gastric cancer), (4) cardiovascular diseases (myocardial fibrosis), (5) bone and articular diseases (e.g., bone marrow fibrosis and rheumatoid arthritis), (6) skin diseases (e.g., post surgical scar, burn scar, keloid, hypertrophic scar and scleroderma), (7) obstetric diseases (e.g., hysteromyoma), (8) urologic diseases (prostatic hypertrophy), (9) other diseases (e.g., Alzheimer's disease, sclerosing peritonitis, type I diabetes and post surgical adhesion). Accordingly, the tissue fibrosis may be cardiac fibrosis, scleroderma, skeletal muscle fibrosis, hepatic fibrosis, kidney fibrosis, pulmonary fibrosis, intestinal fibrosis, or diabetic fibrosis. For example, a fibrosis may be ongenital hepatic fibrosis (CHF); renal tubulointerstitial fibrosis; pulmonary fibrosis associated with an autoimmune disorder (e.g. rheumatoid arthritis, lupus and sarcoidosis); interstitial fibrosis associated with diabetic cardiomyopathy; skeletal muscle fibrosis associated with muscular dystrophies (e.g., Becker muscular dystrophy and Duchenne muscular dystrophy), denervation atrophies, neuromuscular diseases (e.g., acute polyneuritis, poliomyelitis, Werdig/Hoffman disease, amyotrophic lateral sclerosis, progressive bulbar atrophy disease), Mediastinal fibrosis (soft tissue of the mediastinum), myelofibrosis (bone marrow), retroperitoneal fibrosis (soft tissue of the retroperitoneum), progressive massive fibrosis (lungs), nephrogenic systemic fibrosis (skin), Crohn's Disease (intestine), Keloid (skin), scleroderma/systemic sclerosis (skin, lungs), rrthrofibrosis (knee, shoulder, other joints), Peyronie's disease (penis), dupuytren's contracture (hands or fingers), Some forms of adhesive capsulitis (shoulder).

"Hepatic fibrosis" or "fibrosis of the liver" is the excessive accumulation of extracellular matrix proteins including collagen that occurs in most types of chronic liver diseases. Advanced liver fibrosis results in cirrhosis, liver failure, and portal hypertension and often requires liver transplantation. Activated hepatic stellate cells, portal fibroblasts, and myofibroblasts of bone marrow origin have been identified as major collagen-producing cells in the injured liver. These cells are activated by fibrogenic cytokines such as TGF-$\beta$1, angiotensin II, and leptin. The main causes of liver fibrosis in industrialized countries include chronic alcohol abuse, nonalcoholic steatohepatitis (NASH), iron and copper overload, alcohol-induced liver injury, chronic infection of hepatitis C, B, and D, hemochromatosis, secondary biliary cirrhosis, NASH, and autoimmune hepatitis.

"Pulmonary fibrosis" or "fibrosis of the lung" is a respiratory disease in which scars are formed in the lung tissues, leading to serious breathing problems. The accumulation of excess fibrous connective tissue leads to thickening of the walls, and causes reduced oxygen supply in the blood. As a consequence patients suffer from perpetual shortness of breath. Pulmonary fibrosis may be a secondary effect of other diseases. Most of these are classified as interstitial lung diseases. Examples include autoimmune disorders, viral infections and bacterial infection like tuberculosis which may cause fibrotic changes in both lungs upper or lower lobes and other microscopic injuries to the lung. Idiopathic pulmonary fibrosis can also appear without any known cause. Diseases and conditions that may cause pulmonary fibrosis as a secondary effect include: inhalation of environmental and occupational pollutants, hypersensitivity pneumonitis, cigarette smoking, some typical connective tissue diseases (such as rheumatoid arthritis, SLE and scleroderma), other diseases that involve connective tissue (such as sarcoidosis and Wegener's granulomatosis), infections, and certain medications (e.g., amiodarone, bleomycin (pingyangmycin), busulfan, methotrexate, apomorphine, and nitrofurantoin).

"Cardiac fibrosis" or "fibrosis of the heart" may refer to an abnormal thickening of the heart valves due to inappropriate proliferation of cardiac fibroblasts, but more commonly refers to the proliferation of fibroblasts in the cardiac muscle. Fibrotic cardiac muscle is stiffer and less compliant and is seen in the progression to heart failure. Fibrocyte cells normally secrete collagen, and function to provide structural support for the heart. When over-activated this process causes thickening and fibrosis of the valve, with white tissue building up primarily on the tricuspid valve, but also occurring on the pulmonary valve. The thickening and loss of flexibility eventually may lead to valvular dysfunction and right-sided heart failure.

"Renal fibrosis" or "fibrosis of the kidney", characterized by glomerulosclerosis and tubulointerstitial fibrosis, is the final common manifestation of a wide variety of chronic kidney diseases (CKD). Progressive CKD often results in widespread tissue scarring that leads to the complete destruction of kidney parenchyma and end-stage renal failure.

Cystic fibrosis (CF) is a genetic disorder that affects mostly the lungs but also the pancreas, liver, kidneys and intestine. Patients experience symptoms including difficulty breathing and coughing up sputum as a result of frequent lung infections. CF is an autosomal recessive disorder, caused by mutations in both copies of the gene for the protein cystic fibrosis transmembrane conductance regulator (CFTR). CFTR is involved in production of sweat, digestive fluids, and mucus.

A compound of the present application modulates (e.g., inhibits the activity of, decreases the expression of, and/or increases the degradation of) a factor (e.g., collagen, TGF-$\beta$1) that is involved in the regulation of the fibrosis process. For example, a compound of the present application is capable of reducing collagen synthesis. In another example, a compound of the present application can decrease the production of fibrogenic cytokines (e.g., TGF-$\beta$1). In another example, a compound of the present application can reduce the accumulation of extracellular matrix protein. In yet another example, a compound of the present application can inhibit the proliferation of fibroblast cells.

In another example, a compound of the present application may inhibit processes mediated by $\alpha$v integrins. Inhibition and blockade of $\alpha$v$\beta$6 and/or $\alpha$v$\beta$8 result in a phenotype similar to all of the development effects of loss of TGF-$\beta$1 and TFG-$\beta$3, suggesting that these integrins are required for most or all important roles of these TGF-$\beta$ isoforms in development of fibrosis. Antagonists of the integrins $\alpha$v$\beta$6 and/or $\alpha$v$\beta$8 are thus useful for treating and preventing fribrotic activity. For example, TGF-$\beta$ activation by the $\alpha$v$\beta$6 integrin has been shown to play an important role in models of fibrosis in the lungs, biliary tract, and kidney (Henderson et al., *Nat Med* 19, 617 (2013)). The $\alpha$v$\beta$6 integrin has further been shown to be overexpressed in human kidney epithelium in membranous glomerulonephritis, diabetes mellitus, IgA nephropathy, Goodpasture's syndrome, and Alport syndrome renal epithelium (*Am. Journal of Pathology,* 2007). In one aspect, a compound of the present application treats or prevents fibrosis by inhibiting $\alpha$v$\beta$6 and/or $\alpha$v$\beta$8.

Thus, in one aspect, the present application provides a method of treating or preventing a fibrosis, comprising administering to a subject in need thereof a therapeutically effective amount of a compound of the present application or a pharmaceutically acceptable salt or solvate thereof or a therapeutically effective amount of a pharmaceutical composition of the application. In one aspect, the application provides treating a fibrosis. In one aspect, the application provides preventing a fibrosis.

In another aspect, the present application also provides the use of a compound of the present application or a pharmaceutically acceptable salt or solvate thereof in the manufacture of a medicament for the treatment or prevention of a fibrosis in a subject. The present application also provides the use of a compound of the present application or a pharmaceutically acceptable salt or solvate thereof in treating or preventing a fibrosis in a subject.

In one aspect, the fibrosis is fibrosis of the liver, kidney, intestine, lung, or heart. In a further aspect, the fibrosis is involved in various diseases or disorders, such as (1) renal diseases (e.g., tubulointerstitial nephritis), (2) respiratory diseases (e.g., interstitial pneumonia (pulmonary fibrosis)), (3) gastrointestinal diseases (e.g., hepatocirrhosis, chronic pancreatitis and scirrhous gastric cancer), (4) cardiovascular diseases (myocardial fibrosis), (5) bone and articular diseases (e.g., bone marrow fibrosis and rheumatoid arthritis), (6) skin diseases (e.g., post surgical scar, burn scar, keloid, hypertrophic scar and scleroderma), (7) obstetric diseases (e.g., hysteromyoma), (8) urologic diseases (prostatic hypertrophy), (9) other diseases (e.g., Alzheimer's disease, sclerosing peritonitis, type I diabetes and post surgical adhesion).

The dosage regimen utilizing the compounds of the application is selected in accordance with a variety of factors including type, species, age, weight, sex and medical condition of the patient; the severity of the condition to be treated; and the particular compound or salt thereof employed. An ordinary skilled physician, veterinarian or clinician can readily determine and prescribe the effective amount of the drug required to prevent, counter or arrest the progress of the condition.

In the methods of the application, the compounds herein described in detail can form the active ingredient, and are typically administered in admixture with suitable pharmaceutical diluents, excipients or carriers (collectively referred to herein as "carrier") suitably selected with respect to the intended topical administration and consistent with conventional pharmaceutical practices.

For purposes of the application, the following definitions will be used (unless expressly stated otherwise):

"A compound of the application", "compounds of the application", "a compound of the present application", or "compounds of the present application" refers to a compound(s) disclosed herein, e.g., a compound(s) of the application includes a compound(s) of any of the formulae described herein including formula I and/or a compound(s) explicitly disclosed herein. Whenever the term is used in the context of the application it is to be understood that the reference is being made to the free base and the corresponding pharmaceutically acceptable salts or solvates thereof, provided that such is possible and/or appropriate under the circumstances.

"Pharmaceutical" or "pharmaceutically acceptable" when used herein as an adjective, means substantially non-toxic and substantially non-deleterious to the recipient.

By "pharmaceutical composition" it is further meant that the carrier, diluent, solvent, excipient, and salt must be compatible with the active ingredient of the formulation (e.g., a compound of the application). It is understood by those of ordinary skill in this art that the terms "pharmaceutical formulation" and "pharmaceutical composition" are generally interchangeable, and they are so used for the purposes of this application.

"Solution" refers to a clear, homogeneous liquid dosage form that contains one or more chemical substances dissolved in a solvent or mixture of mutually miscible solvents. Because molecules of a therapeutic agent substance in solution are uniformly dispersed, the use of solutions as dosage forms generally provides assurance of uniform dosage upon administration and good accuracy when the solution is diluted or otherwise mixed. "Solution" as disclosed herein contemplates any variations based on the current state of the art or variations achieved by one skilled in the art.

"Suspension" refers to a liquid dosage form that contains solid particles dispersed in a liquid vehicle. "Suspension" as disclosed herein contemplates any variations based on the current state of the art or variations achieved by one skilled in the art.

"Excipient" is used herein to include any other compound that is not a therapeutically or biologically active compound and may be contained in or combined with one or more of the compounds of the present application. As such, an excipient should be pharmaceutically or biologically acceptable or relevant (for example, an excipient should generally be non-toxic to the subject). "Excipient" includes a single such compound and is also intended to include a plurality of excipients. For the purposes of the present disclosure the term "excipient" and "carrier" are used interchangeably throughout the description of the present application.

"Therapeutically effective amount" refers to that amount of a drug or pharmaceutical agent that will elicit the biological or medical response of a tissue, system, animal, or human that is being sought by a researcher or clinician.

"Treat," "treating," or "treatment" refers to decreasing the symptoms, markers, and/or any negative effects of a disease or condition in any appreciable degree in a subject who currently has the disease or condition. In some embodiments, treatment may be administered to a subject who exhibits only early signs of a disease or condition for the purpose of decreasing the risk of developing the disease or condition. In some embodiments, "Treat," "treating," or "treatment" refers to amelioration of one or more symptoms of a disease or condition. For example, amelioration of one or more symptoms of a disease or condition includes a decrease in the severity, frequency, and/or length of one or more symptoms of a disease or condition.

"Prevent," "prevention," or "preventing" refers to any method to partially or completely prevent or delay the onset of one or more symptoms or features of a disease or condition. Prevention may be administered to a subject who does not exhibit any sign of a disease or condition.

"Subject" means a human or animal (in the case of an animal, more typically a mammal). In one aspect, the subject is a human. In some embodiments, a subject in the present application is in need of a treatment and/or prevention of a disease described herein.

The term "symptom" is defined as an indication of disease, illness, injury, or that something is not right in the body. Symptoms are felt or noticed by the individual experiencing the symptom, but may not easily be noticed by others. Others are defined as non-health-care professionals.

"αv integrin antagonist" refers to a compound which binds to and inhibits or interferes with the function of one or more of αvβ3, αvβ5, αvβ6, and αvβ8, a compound which binds to and inhibits or interferes with the function of both αvβ3 and αvβ5 (i.e., a dual αvβ3/αvβ5 antagonist), or a compound which binds to and inhibits or interferes with the function of both αvβ6 and αvβ8 (i.e., a dual αvβ6/αvβ8 antagonist). The compounds bind to the receptors as antagonists, blocking or interfering with the binding of the native agonist, such as vitronectin, while not provoking a biological response themselves.

"Alkyl" refers to straight chain or branched alkyl of the number of carbon atoms specified (e.g., $C_1$-$C_4$ alkyl), or any number within this range (methyl, ethyl, propyl, i-propyl, butyl, i-butyl, t-butyl, etc.).

"Alkoxy" refers to straight chain or branched alkoxides of the number of carbon atoms specified (e.g., $C_1$-$C_6$ alkoxy), or any number within this range (methoxy, ethoxy, propoxy, i-propoxy, butoxy, i-butoxy, t-butoxy, etc.).

"Carbocyclic ring" refers to saturated cycloalkyl of the number of carbon atoms specified (i.e., $C_3$ or $C_4$), such as cyclopropyl and cyclobutyl.

"Heterocyclic ring" refers to saturated heterocyclic ring of the number of carbon atoms specified (i.e., $C_3$ or $C_4$), further comprising one additional heteroatoms selected from N and O.

The term "about" refers to a range of values which can be 15%, 10%, 8%, 5%, 3%, 2%, 1%, or 0.5% more or less than the specified value. For example, "about 10%" can be from 8.5% to 11.5%. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

EXAMPLES

Example 1

Testing of the Compounds of Present Application in Cell Adhesion Assays

The ability of compounds to block adhesion of three primary cell cultures: human dermal microvascular endothelial (HMVEC), rat lung microvascular endothelial (RLMVEC), and rabbit aortic endothelial (RAEC) cells, to vitronectin coated plates was determined using the following procedure. This test demonstrates inhibition of the interaction of αv integrin on the cell surface with the ligand, vitronectin.

Adhesion plates preparation. 96-well plates were coated with vitronectin in PBS, pH 7.4 by incubating 50 μL of the solution (10 μg/ml) for 1.5 h at room temperature or overnight at 4° C. The plates then were blocked with 1% BSA in PBS (30 min at room temperature) and washed with PBS.

Cell culturing and loading. HMVEC cells (passages (p)9-14) (from Lonza, Allendale, N.J.) RLMVEC cells (p4-14) (from Vec Technology, Rensselaer, N.Y.) and RAEC cells (p4-14) (from CellBiologics, Chicago, Ill.) were used for the compound testing. Cells were grown in T175 tissue culture flasks and dislodged by gentle 3 min treatment with Accutase (Life Technologies). After washing, the cells in suspension in RPMI-1640 (Life Technologies) were loaded with calcein-AM (5 μM) (Life Technologies) for 30 min at 37° C. and re-suspended into RPMI w/o phenol red medium containing 10% FBS.

Adhesion assay. The cell suspension was aliquoted into the wells at a density of $1.0 \times 10^5$ cells/well (RLMVEC) and $5.0 \times 10^4$ (HMVEC, and RAEC). The test compounds were added at the same time with the cells. The plates were incubated for 1.5 h at 37° C. The cells that did not adhere during this incubation were removed by gentle washing. The wash was performed by 2 cycles of aspiration of the supernatant and addition of 100 μL of the pre-warmed fresh DPBS (Life Technologies). A fluorescence of the remaining cells was measured using multimode plate reader (Victor 2V, PerkinElmer) at an excitation/emission wavelengths of 485/535 nm. The compounds were tested starting with maximal concentration of 1 μM with half-log dilution schedule. $IC_{50}$ values were calculated with Prism 5 (GraphPad, CA) by fixing the bottom of the curves to a value of blank for empty wells fluorescence.

Example 2

Anti-angiogenic Activity Using Chick Chorioallantoic Membrane (CAM) Assay

CAM surfaces were grafted with gelatin sponges impregnated with the concentrations of test compounds and 50 ng VEGF dissolved in PBS. Untreated CAM received only VEGF and PBS. Error bars represent SEM, N=5, P values for the treated groups were calculated by comparing with the untreated group (*$p<0.05$,$p<0.01$,*$p<0.001$).

Test substance preparation: Test samples and standards were dissolved in PBS and sterilized by passing through a syringe filter (0.22 μm). hVEGF (SIGMA) 50 ng/μl was prepared in sterile PBS.

Grafting: Gelatin sponge (Abogel) was cut in approximately 2 $mm^3$ pieces and loaded with required test substance or PBS and VEGF. The graft was placed on the CAM.

Eggs: Fertile hen eggs were procured from a hatchery and were cleaned and decontaminated using alcohol. 1 ml of albumin was removed using a syringe and incubated for 8 days. Grafts were placed on developing CAMs and further incubated to day 12. On day 12, CAMs were fixed with 4% formaldehyde in PBS, dissected and imaged.

Imaging: Fixed CAMs were imaged under constant illumination and magnification under a stereomicroscope fitted with a digital camera (CANON).

Image analysis: Images were analyzed on MS PowerPoint keeping the image size constant. A ring was drawn around the graft and the size was kept constant. Blood vessels crossing the ring were counted for each test group.

Statistical Analysis:Data were analyzed on MSExcel 2007.

Example 3

Distribution in Plasma in Dutch Belted Rabbits

The plasma concentrations of compounds of the present application were determined following administration in Dutch Belted rabbits. The test compounds were administered at a concentration of 1.0-2.5 mg/mL. Plasma samples were collected at pre-determined time points. Also, weights were recorded. Plasma sample concentrations of the compounds were determined by LC-MS/MS.

Animal Dosing: The exposure of compounds was evaluated in Dutch Belted rabbits. The study was not blinded. Each compound was dosed as n=3/time point for a total of nine rabbits. Rabbits were housed one per cage. Animals were not fasted, and food and water were supplied ad libitum.

Animals were anesthetized following the 13IA5 IACUC protocol for the dosing. Each rabbit received a bolus dose of test formulation at time zero on the day of dosing. Plasma samples were collected at pre-determined time points. Animals for the 30-minute and 1-hour time points were anesthetized for the entire duration of the study. The animals for the 8-hour time point were recovered after dosing and then euthanized for sampling purposes.

At each time point, approximately 0.5 mL of blood was collected and placed into chilled Na-heparin tubes containing citric acid. Blood samples were centrifuged at a speed of 3,000 g for 5 minutes to obtain plasma as quickly as possible. Samples were stored frozen at −80° C. until analysis.

Analysis of Plasma Samples: An LC-MS/MS method was developed for the determination of compounds of the present application in rabbit plasma samples. A pre-study standard curve was analyzed to determine the specificity, range, and lower limit of quantitation of the method.

Example 4

Diagnosing Fibrosis

Fibrosis is a pathophysiological process in response to tissue injury due to viral or bacterial infection, inflammation, autoimmune disease, trauma, drug toxicity, and so on. During this process, an excess amount of collagen is expressed and fibrous material forms in the extracellular space of the affected tissue. Thus, fibrosis can be generally recognized based on the distinct morphology of fibrous tissue in a biopsy of the organ in which fibrosis is suspected. Other means for detecting the presence of fibrosis or developing fibrosis include computerized axial tomography (CAT or CT) scan, ultrasound, magnetic resonance imaging (MRI), and monitoring the level of one or more serum markers known to be indicative of fibrosis (e.g., various types of collagens).

The precise manner of diagnosing fibrosis also varies depending on the organ where the fibrotic process takes place. For instance, biopsies are generally effective for diagnosing fibrosis of most organs, whereas endoscopy involving a fiber optic instrument (e.g., a sigmoidoscope or a colonoscope) can be a less traumatic alternative to detect fibrosis of certain organs such as the intestine.

Biopsy for Detecting Fibrosis

Standard procedures have been established for obtaining biopsy from a given organ or tissue. For example, a specimen can be obtained during exploratory surgery, but is more often obtained by inserting a biopsy needle through the skin and into the organ or tissue. Before this procedure is performed, the person receives a local anesthetic. Ultrasound or CT scans may be used to locate the abnormal area from which the specimen is to be taken.

Upon obtaining an organ or tissue biopsy, the sample is examined and given a score to indicate the presence and level of fibrosis in the sample. Most frequently used scoring systems include the METAVIR or modified HAI (ISHAK) scoring system. The Knodell scoring system can also be used for analyzing the liver sample. The criteria used in scoring are well established and known to those of skilled in the art. For example, the METAVIR system provides five gradings: FO indicates the absence of fibrosis; F1 indicates portal fibrosis without septa; F2 indicates portal fibrosis and some septa; F3 indicates septal fibrosis without cirrhosis; and F5 indicates the presence of cirrhosis.

Biopsy is not only useful for the diagnosis of fibrosis, it can also aid physicians to assess the effectiveness of fibrosis treatment/prevention methods of the present application by monitoring the progression of fibrosis using methodologies known in the art. See, e.g., Poynard et al., *Lancet* 349:825, 1997.

Fibrosis Markers

There are numerous known serum markers whose level can be indicative of the presence and/or severity of fibrosis. Blood tests measuring markers, e.g., hyaluronic acid, laminin, undulin (type IV collagen) pro-peptides from types I, II, and IV collagens, lysyl oxidase, prolyl hydroxylase, lysyl hydroxylase, PIIINP, PICP, collagen VI, tenascin, collagen XIV, laminin P1, TIMP-1, MMP-2, α2 macroglobulin, haptoglobin, gamma glutamyl transpeptidase, γ globulin, total bilirubin, apolipoprotein A1, etc., according to the established methods can thus be useful for both the diagnosis of fibrosis and monitoring of fibrosis progression. Additional markers, such as nucleic acid markers, can be used for detecting and/or monitoring fibrosis. For instance, Wnt-4 has recently been indicated in laboratory experiments as a gene that plays an important role in renal fibrosis, where its mRNA expression is significantly increased in the fibrotic tissue in the kidney (See, e.g., Surendran et al., *Pediatr.* 140:119-24, 2002). The quantitative detection of gene expression of this type of markers can be useful in the diagnosis and monitoring of fibrosis.

Example 5

Animal Models of Fibrosis—Lung Fibrosis

Lung fibrosis is induced in 150-g male Sprague-Dawley rats (Charles River Laboratories) with an intratracheal instillation of 100 µl of 10 U/ml bleomycin, or alternatively, in 20-g male C57BL/6 mice (The Jackson Laboratory) with an intratracheal instillation of 60 µl of bleomycin (3 U/kg). Rats are injected with an i.p. injection of a solution or suspension of a compound of formula I or an equal volume of sodium phosphate buffer the day after bleomycin treatment and again on days 3, 5, 7, and 9. Mice are treated daily, starting the day after bleomycin injection, with an i.p. injection of either a solution or suspension of a compound of formula I or an equal volume of sodium phosphate buffer.

Measurement of Peripheral Blood Oxygen Content

To assess peripheral blood oxygen content in vivo, rats are monitored for the percentage of hemoglobin saturated with oxygen (pulse Ox). Rats are briefly sedated with 4% isoflurane in 4 L/min oxygen. Rats are then removed to room air, and a peripheral pulse Ox sensor is attached to the left rear paw. Pulse Ox readings are taken as the animal regains consciousness.

Quantification of Collagen

Rats and mice are euthanized at day 14 or 21 after bleomycin instillation, and the lungs are perfused by injections of PBS into the right ventricle of the heart to remove blood. For rats, the whole right lung is removed, weighed, and minced into small pieces, and whole lung collagen content is assessed by the Sircol collagen assay (Biocolor), according to the manufacturer's instructions. For mice, collagen is assessed on formalin-fixed paraffin-embedded sections of whole lung. Briefly, 15-µm sagittal (longitudinal from top to bottom) sections are cut, and 10 sections from across the lung are used to quantify collagen content. Sections are deparaffinized, and then incubated for 30 min at room temperature with a saturated solution of picric acid in distilled water containing 0.1% fast green FCF and 0.1% Sirius red F3BA (Polysciences). Sections are repeatedly rinsed with distilled water, and the dye is eluted with a mixture of 0.1 N NaOH and absolute methanol (1:1, v/v). Spectrophotometer readings are taken at 540 and 605 nm (corresponding to the maximum absorbance of Sirius red and fast green, respectively). The absorbances are used to calculate the amount of collagen and noncollagenous protein in the samples. Collagen content is expressed as a percentage of total protein.

Example 6

Animal Model of Fibrosis—Liver Fibrosis

In a standardized liver fibrosis model, mice are treated with 1.0 mL/kg CCl4 three times per week for 11 consecutive weeks, and levels of serum markers (AST, ALT, bilirubin, and albumin), expression of fibrosis marker genes (using quantitative reverse transcription polymerase chain reaction [RT-PCR]), histopathology (using Hematoxylin and eosin staining), and connective tissue formation (using Massive trichrome staining) are analyzed. The outcomes show that serum markers and the levels of fibrosis marker genes are significantly increased in the standardized liver fibrosis model. Additionally, sharp increases in fibronectin and pro-collagen expression, and the development of cirrhosis (fibrosis stage 3-5/6) in liver tissues of the standardized mouse model of hepatic fibrosis are observed. Compounds of formula I are tested in this model for preventing or treating liver fibrosis by administering a solution or suspension i.p. of by oral gavage.

Example 7

Testing of the Compounds of Present Application in $\alpha_v$ Integrin Binding Assays All $\alpha_v$ Integrins are known to bind to proteins with a RGD motif. Two RGD ligands were used in this study: Vitronectin (VN) as a ligand for $\alpha_v\beta_3$ and $\alpha_v\beta_5$ (Wayner et al., *J. Cell Biol.*, 113 (4), 919-929, 1991), and LAP TGF-β1 (LAP1) as a ligand for $\alpha_v\beta_6$ and $\alpha_v\beta_8$ (Rognoni et al., *Nat. Med.*, 20(4): 350-359, 2014). CWHM12 was used as a positive control for $\alpha_v\beta_6$ and $\alpha_v\beta_8$ (Henderson et al., *Nat. Med.* 19(12), 10.1038/nm. 3282 2013), and Cilengitide as a positive control for $\alpha_v\beta_3$ and $\alpha v\beta_5$ (Kumar et al., *J. Pharmacol. Exp. Ther.*, 283, 843-853, 1997).

The integrin coupled Dyna beads were allowed to interact with respective ligands. The integrin-ligand complex was detected with either Primary/Secondary Antibody conjugated with Fluorescein Isothiocyanate (FITC). For $\alpha_v\beta3$ and $\alpha_v\beta5$, Vitronectin was used as a ligand and a primary antibody conjugated with FITC (Anti-VN-FITC Ab) was used to detect the interaction. For $\alpha_v\beta6$ and $\alpha_v\beta8$, LAP-TGF β1 was used as ligand and a primary antibody against LAP1 (Anti-LAP1 Ab) and a secondary antibody conjugated with FITC were used to detect the $\alpha_v\beta6/\alpha_v\beta8$-LAP-TGF β1 complex. Fluorescence was measured by Flow Cytometry analysis.

Activation of Beads. 5 mg of Dyna beads were weighed in a low protein binding microfuge (Eppendorf) tube (1.5 mL volume). The beads were re-suspended in 1 mL of Sodium Phosphate Buffer and vortexed at high speed for 30 seconds. The tube was then placed in a tube roller and tilt rotated for 10 min. After tilt rotation, the tube was placed on the Magna Spin and the beads were allowed to settle. The supernatant was discarded and the beads were washed three times. The beads were then re-suspended in 100 μL of Sodium Phosphate Buffer and 20 μL of washed beads were distributed into 5 low protein binding Eppendorf tubes (1 mg of beads in each tube). The beads were used for coupling integrins.

Coupling of Dyna Beads with Integrins. 20 μL of (1 mg) of beads were mixed with 20 μL of integrins (20 g) and 20 μL of 3 M Ammonium Sulfate solution (final concentration of ammonium sulfate was 1M) to achieve a Bead: Protein ratio of 5 mg:100 μg. The solution was mixed gently and placed in a tube roller and incubated at 37° C. for 16 hours.

Quantification of Coupling. The tubes were taken out and subjected to a quick spin. The tubes were placed in the magna spin and the supernatant (60 μL) was collected (Supernatant). The beads were re-suspended in 60 μL of PBS and vortexed for 10 seconds. The beads were allowed to settle in the magna spin and the supernatant was collected as Wash 1 (W1) to remove the loosely bound proteins. The beads were washed three more times with 30 μL of PBS each time, and the supernatant was collected as W2, W3 and W4. The beads were finally re-suspended in 25 μL of PBS and stored at 4° C. until use. The amount of protein bound to beads was quantified by measuring the sum of protein left in the Supernatant, W1, W2, W3 and W4 through the Micro BCA method.

Micro BCA Method. BSA was used as standard. The concentration range of BSA was 1 μg/mL to 20 μg/mL in PBS. 10 μL of the Supernatant was mixed with 40 μL of PBS in a 96 well plate, and then with 100 μL of Micro BCA reagent. The plate was shaked at 37° C. for 3 hours. After incubation, the OD at 562 nm was measured to determine the amount of protein in the Supernatant. The amounts of protein in W1, W2, W3 and W4 were determined with the same procedure.

The amounts of protein in the Supernatant, W1, W2, W3 and W4 were added and subtracted from the initial amount of the protein that was used for beads coupling, which provided the amount of protein bound to the beads and molarity of the protein was calculated.

αVβ6/αVβ8—LAP-TGF β1 interaction: αVβ6/αVβ8 coupled beads were treated with the ligand LAP TGF-β1 (LAP1) at room temperature for 3 hours. The complex (Integrin+Ligand) was then treated with primary Ab (Anti-LAP1 Ab) overnight at 4° C. The whole complex (Integrin+Ligand+Primary Ab) was treated with Secondary Ab conjugated with FITC and incubated for 2 hours. The complex was analyzed by either plate reader or Flow Cytometer.

10 μL of αVβ6/αVβ8 coupled beads were taken for the experiment. The concentration of integrins was 10 nM. 10 μL of LAP1 was taken (10 nM for αVβ6 and 20 nM for αVβ8). Reaction between integrin coupled beads and LAP1 was considered as the full reaction, and reaction without LAP1 or a compound of the disclosure was considered as the blank reaction. The samples were incubated in low protein binding tubes at room temperature for 3 hours. The tubes were briefly spun and placed in a Magna spin. The supernatant was removed. The beads were washed with assay buffer twice to remove excess LAP1 and then re-suspended in 150 μL of assay buffer containing 1:200 anti-LAP1 Ab (primary Ab). The tubes were placed in a tube roller and incubated at 4° C. overnight. After a brief spin, the tubes were then placed in a Magna spin and the supernatant was removed. The beads were washed with assay buffer twice to remove excess primary Ab and then re-suspended in 150 μL of assay buffer containing 1:500 secondary Ab conjugated with FITC. The tubes were incubated at room temperature for 2 hours in a tube roller. After a brief spin, the tubes were placed in a Magna spin and the supernatant was removed. The beads were washed with assay buffer twice followed by PBS. The beads were then re-suspended in 300 μL of PBS and analyzed by a Flow Cytometer (BD FACSCalibur, Software—BDcell Quest Pro Version 6).

αVβ3/αV5—LAP-TGF β1 interaction: αVβ3/αVβ5 coupled beads were treated with the ligand at room temperature for 3 hours. The complex (Integrin+Ligand) was then treated with Anti-Vitronectin Ab conjugated with FITC overnight at 4° C. The complex was analyzed by either plate reader or Flow Cytometer.

10 μL of αVβ3/αVβ5 coupled beads were taken for the experiment. The concentration of integrins was 10 nM. 10 μL of vitronectin was taken. The concentration was 10 nM. Reaction between integrin coupled beads and vitronectin was considered as the full reaction, and reaction without vitronectin or a compound of the disclosure was considered as the blank reaction. The samples were incubated in low protein binding tubes at room temperature for 3 hours. The tubes were briefly spun and placed in a Magna spin. The supernatant was then removed. The beads were washed with assay buffer twice to remove excess vitronectin and then re-suspended in 150 μL of assay buffer containing 1:500 Anti-vitronectin Ab conjugated with FITC. The tubes were placed in a tube roller and incubated at 4° C. overnight. After a brief spin, the tubes were placed in a Magna spin and the supernatant was discarded. The beads were washed with assay buffer twice followed by PBS. The beads were then re-suspended in 300 μL of PBS and analyzed by a Flow Cytometer (BD FACSCalibur, Software—BD Cell Quest Pro Version 6).

Quantification: The samples were acquired using a BD FACSCalibur system and analyzed with BD Cell quest pro Version 6. Median values for the following were extracted from the software: Full reaction (Integrin+Ligand) with or without compound, Control: Without Ligand (LAP1/Vitronectin), and Vehicle Control: Full reaction with DMSO. Blank=Test Median value−control Median value. Percentage Inhibition=100−[(Blanked Test Median/Blanked vehicle Median)*100]. Percentage of binding was calculated with respect to full reaction. The value was subtracted from 100 to get percentage of inhibition. All the plotted values were average of triplicates. SD was determined for each experiment. $IC_{50}$ was determined with Graph Pad Prism.

Inhibition of Integrin-Ligand interaction by reference inhibitors: The optimized protocol was validated by employing reference compounds such as Cilengitide (αVβ3/αVβ5–VN interaction) and CWHM12 (αVβ6/αVβ8–LAP1 interaction). The full reaction (Integrin-Ligand Interaction) was optimized as above. Integrin coupled beads were taken for the experiment.

2 μL of 10 nM/20 nM of Ligand was taken and mixed with 8 μL of the compound (i.e., Cilengitide or CWHM12, each diluted from a 10 mM stock). Reaction, with or without DMSO (0.08%), between Integrin and Ligand in the absence of the compound was considered as the full reaction. Reaction with DMSO (0.08%) in the absence of compound and Ligand was considered as the blank reaction.

The samples incubated in low protein binding tubes at room temperature for 3 hours. The tubes were placed in a Magna spin and the supernant was discarded. The beads were washed with assay buffer twice to remove the excess Ligand and then re-suspended in 150 μL of assay buffer containing the primary antibody (1:500 of Anti-VN-FITC or 1:200 of Anti-LAP1 Ab). The tubes were placed in a tube roller and incubated at 4° C. overnight. After a brief spin, the tubes were placed in a Magna spin, and the supernatant was discarded. In the case of αVβ3/αVβ5–VN interaction, the beads were washed with assay buffer twice and finally washed with PBS. The beads were then re-suspended in 300 μL of PBS and analyzed by a Flow Cytometer. In the case of αVβ6/αVβ8—LAP1 interaction, the beads were washed with assay buffer twice and treated with 150 μL of Secondary Antibody (1:500) for two hours at room temperature, washed twice with assay buffer and PBS, and finally re-suspended in 300 μL of PBS and analyzed by a Flow Cytometer.

Table 2 shows the integrin inhibition activity of compounds of the application.

TABLE 2

Integrin Inhibition Assay Results

| Cmpd # | αvβ6 $IC_{50}$ (nM) | αvβ8 $IC_{50}$ (nM) | αvβ8/αvβ6 |
|---|---|---|---|
| A1 | 9.57 | 17.56 | 1.83 |

EQUIVALENTS

Those skilled in the art will recognize, or be able to ascertain using no more than routine experimentation, many equivalents to the specific embodiments and methods described herein. Such equivalents are intended to be encompassed by the scope of the present application.

All patents, patent applications, and literature references cited herein are hereby expressly incorporated by reference.

The invention claimed is:
1. A method of treating or preventing a fibrosis, comprising administering to a subject in need thereof a therapeutically effective amount of a compound of formula I:

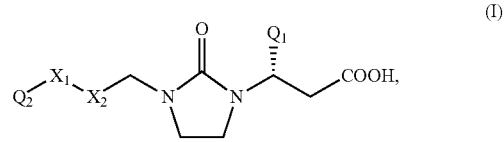

or a pharmaceutically acceptable salt or solvate thereof, wherein:
$X_1$-$X_2$ is $CHR_1$—$CH_2$, CH=CH, or C(O)—$CH_2$;
$R_1$ is H or OH;
$Q_1$ is

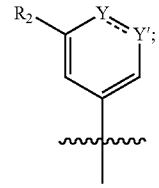

Y=Y' is $CR_3$=N, $CR_4$=$CR_4$, or C(O)—NH;
$R_3$ is $C_1$-$C_3$ alkoxy, F, or $R_3$, together with $R_2$ and the carbon atoms to which they are attached, form a phenyl ring;
each $R_4$ is independently $C_1$-$C_3$ alkoxy, F, or two $R_4$, together with the carbon atoms to which they are attached, form a 5- or 6-membered heterocyclic ring comprising one or two heteroatoms selected from N and O;
$R_2$ is H or together with $R_3$ and the carbon atoms to which they are attached, form a phenyl ring; and
$Q_2$ is

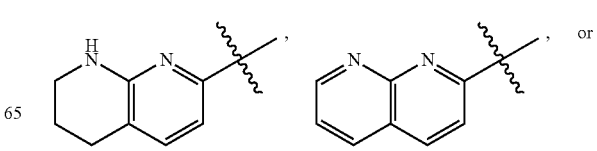

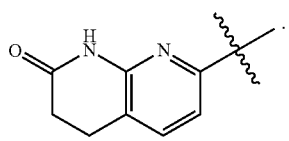 [SMILES: *c1ccc2c(n1)NC(=O)CC2]

2. The method of claim 1, wherein $X_1$-$X_2$ is $CHR_1$—$CH_2$.
3. The method of claim 2, wherein $R_1$ is H.
4. The method of claim 2, wherein $R_1$ is OH.
5. The method of claim 1, wherein $X_1$-$X_2$ is CH=CH.
6. The method of claim 1, wherein $X_1$-$X_2$ is C(O)—$CH_2$.
7. The method of claim 1, wherein Y⹀Y' is $CR_3$=N.
8. The method of claim 7, wherein $R_3$ is methoxy, ethoxy, or propoxy.
9. The method of claim 7, wherein $R_3$, together with $R_2$ and the carbon atoms to which they are attached, form a phenyl ring.
10. The method of claim 1, wherein Y⹀Y' is $CR_4$=$CR_4$.
11. The method of claim 10, wherein one of $R_4$ is methoxy, ethoxy, or propoxy.
12. The method of claim 10, wherein two $R_4$, together with the carbon atoms to which they are attached, form a 5- or 6-membered heterocyclic ring comprising one or two heteroatoms selected from N and O.
13. The method of claim 1, wherein Y⹀Y' is C(O)—NH.
14. The method of claim 1, wherein $Q_2$ is

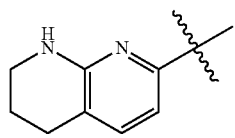

15. The method of claim 1, wherein $Q_2$ is

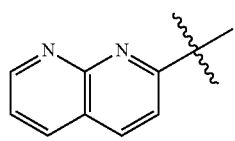

16. The method of claim 1, wherein $Q_2$ is

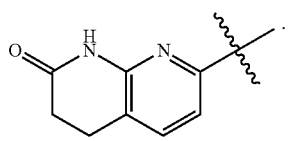

17. The method of claim 1, wherein the compound is selected from:

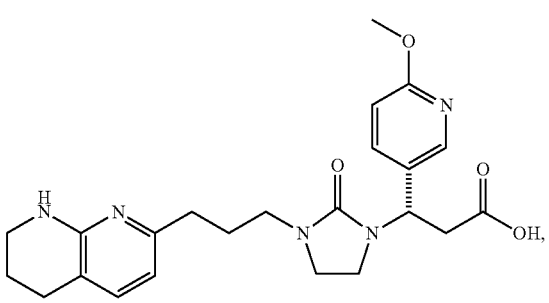

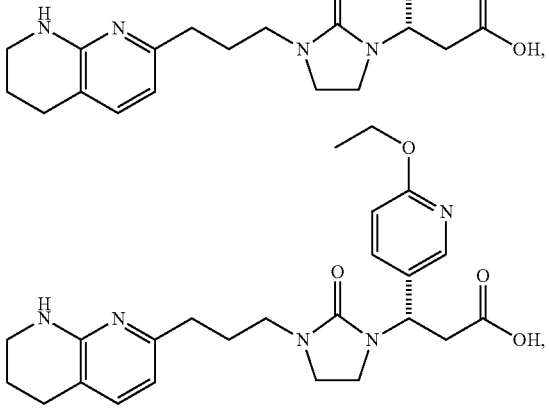

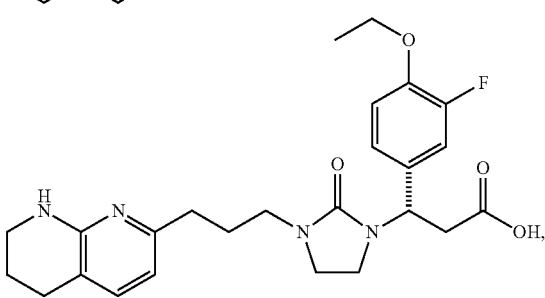

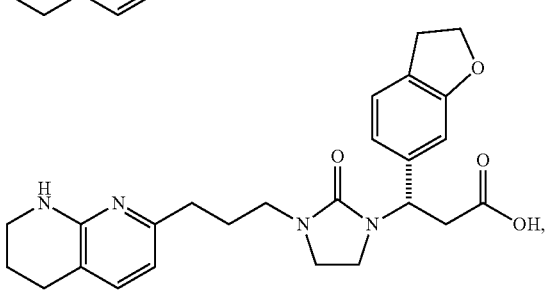

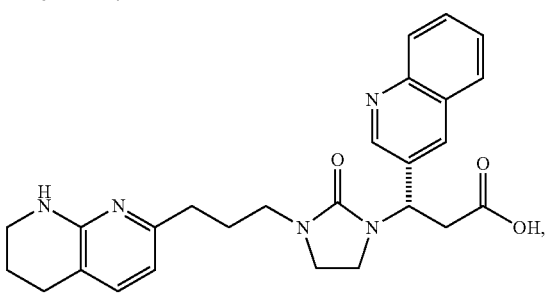

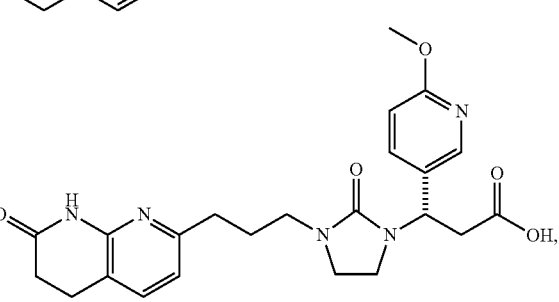

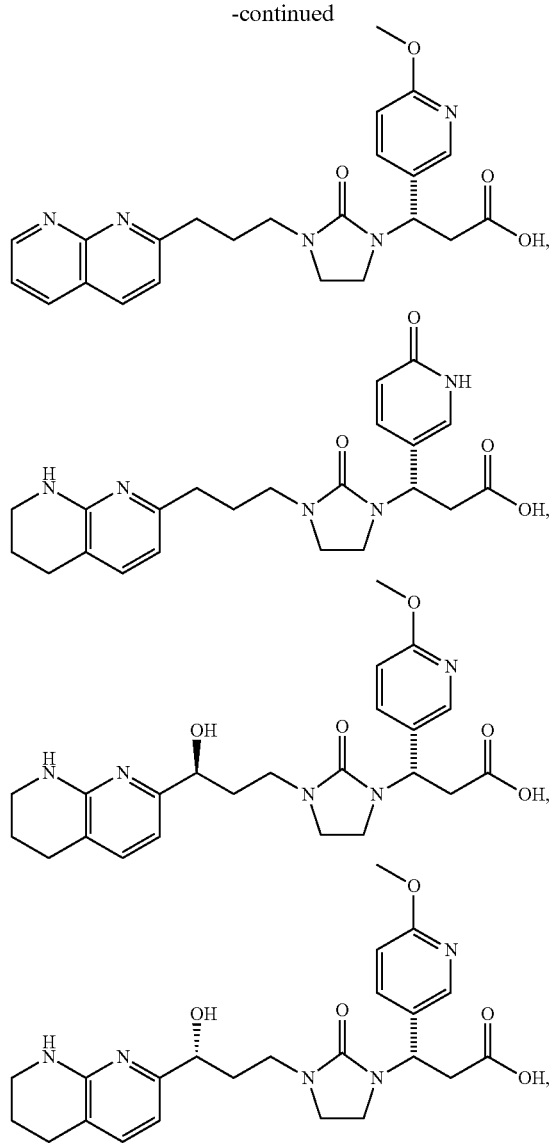
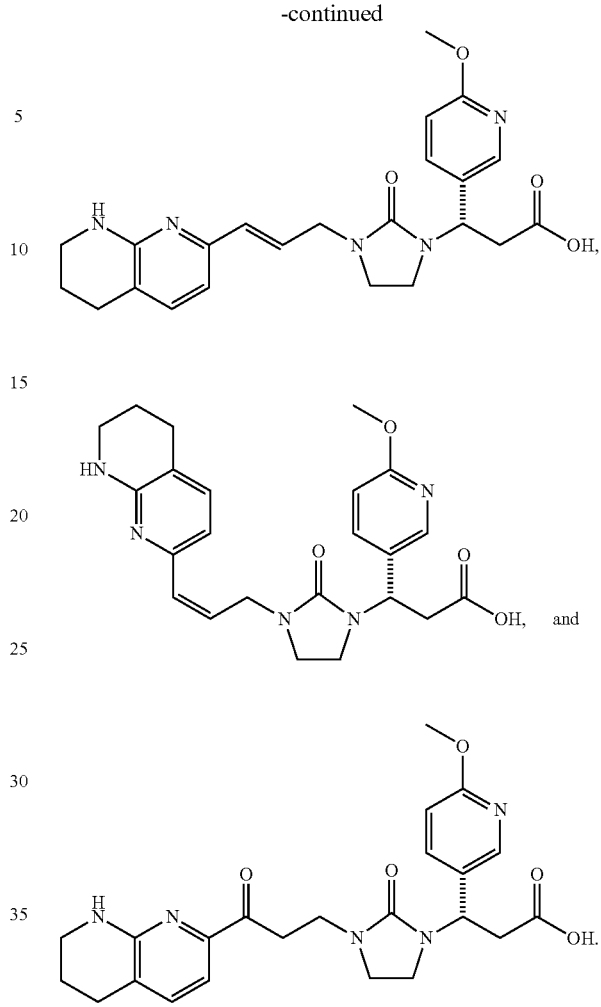
18. The method of claim 1, wherein the fibrosis is hepatic fibrosis, pulmonary fibrosis, cardiac fibrosis, renal fibrosis, or cystic fibrosis.
* * * * *